(12) United States Patent
Yasunami

(10) Patent No.: US 8,470,316 B2
(45) Date of Patent: Jun. 25, 2013

(54) AGENTS FOR SUPPRESSING DAMAGE TO TRANSPLANTED ISLETS AFTER ISLET TRANSPLANTATION

(75) Inventor: Yohichi Yasunami, Fukuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 402 days.

(21) Appl. No.: 12/090,061

(22) PCT Filed: Oct. 13, 2006

(86) PCT No.: PCT/JP2006/320441
§ 371 (c)(1),
(2), (4) Date: Mar. 6, 2009

(87) PCT Pub. No.: WO2007/043641
PCT Pub. Date: Apr. 19, 2007

(65) Prior Publication Data
US 2009/0220499 A1 Sep. 3, 2009

(30) Foreign Application Priority Data
Oct. 14, 2005 (JP) ................. 2005-300489

(51) Int. Cl.
*A61K 39/395* (2006.01)
*A61K 39/00* (2006.01)

(52) U.S. Cl.
USPC ............ 424/130.1; 424/133.1; 424/135.1; 424/141.1; 424/142.1; 424/143.1

(58) Field of Classification Search
None
See application file for complete search history.

(56) References Cited

U.S. PATENT DOCUMENTS

| | | | |
|---|---|---|---|
| 5,216,128 A | 6/1993 | Novick et al. | |
| 5,530,101 A | 6/1996 | Queen et al. | |
| 5,621,077 A | 4/1997 | Novick et al. | |
| 5,639,455 A | 6/1997 | Shimamura et al. | |
| 5,670,373 A | 9/1997 | Kishimoto | |
| 5,795,965 A | 8/1998 | Tsuchiya et al. | |
| 5,817,790 A | 10/1998 | Tsuchiya et al. | |
| 5,856,135 A | 1/1999 | Tsuchiya et al. | |
| 5,888,510 A | 3/1999 | Kishimoto et al. | |
| 6,074,643 A | 6/2000 | Barbera-Guillem | |
| 6,121,423 A | 9/2000 | Tsuchiya et al. | |
| 6,261,560 B1 | 7/2001 | Tsujinaka et al. | |
| 6,552,083 B1 | 4/2003 | Isobe et al. | |
| 6,723,319 B1 | 4/2004 | Ito et al. | |
| 7,291,721 B2 | 11/2007 | Giles-Komar et al. | |
| 7,320,792 B2 | 1/2008 | Ito et al. | |
| 7,414,024 B2 | 8/2008 | Blay et al. | |
| 7,479,543 B2 | 1/2009 | Tsuchiya et al. | |
| 7,521,052 B2 | 4/2009 | Okuda et al. | |
| 7,781,617 B2 * | 8/2010 | Kudou et al. | 564/336 |
| 7,824,674 B2 | 11/2010 | Ito et al. | |
| 8,226,611 B2 | 7/2012 | Chen et al. | |
| 2001/0001663 A1 | 5/2001 | Kishimoto et al. | |
| 2002/0119150 A1 | 8/2002 | Kirk et al. | |
| 2004/0170626 A1 | 9/2004 | Schuurman et al. | |
| 2005/0096257 A1 | 5/2005 | Shima et al. | |
| 2005/0142635 A1 | 6/2005 | Tsuchiya et al. | |
| 2005/0158317 A1 | 7/2005 | Blay et al. | |
| 2006/0039902 A1 * | 2/2006 | Young et al. | 424/133.1 |
| 2006/0165696 A1 | 7/2006 | Okano et al. | |
| 2006/0188502 A1 | 8/2006 | Giles-Komar et al. | |
| 2006/0193772 A1 | 8/2006 | Ochiai et al. | |
| 2006/0251653 A1 | 11/2006 | Okuda et al. | |
| 2007/0036785 A1 | 2/2007 | Kishimoto et al. | |
| 2007/0134242 A1 | 6/2007 | Nishimoto et al. | |
| 2007/0167425 A1 | 7/2007 | Nakade et al. | |
| 2008/0081041 A1 | 4/2008 | Nemeth | |
| 2009/0022719 A1 | 1/2009 | Mihara et al. | |
| 2009/0220500 A1 | 9/2009 | Kobara | |
| 2009/0263384 A1 | 10/2009 | Okada et al. | |
| 2009/0269335 A1 | 10/2009 | Nakashima et al. | |
| 2010/0008907 A1 | 1/2010 | Nishimoto et al. | |
| 2010/0034811 A1 | 2/2010 | Ishida | |
| 2010/0061986 A1 | 3/2010 | Takahashi et al. | |
| 2010/0298542 A1 | 11/2010 | Igawa et al. | |
| 2011/0098450 A1 | 4/2011 | Igawa et al. | |
| 2011/0111406 A1 | 5/2011 | Igawa et al. | |
| 2011/0150869 A1 | 6/2011 | Mitsunaga et al. | |
| 2011/0245473 A1 | 10/2011 | Igawa et al. | |
| 2012/0045453 A1 | 2/2012 | Chen et al. | |
| 2012/0183539 A1 | 7/2012 | Maeda | |

FOREIGN PATENT DOCUMENTS

| | | |
|---|---|---|
| CN | 1164194 | 11/1997 |
| CN | 1297357 | 5/2001 |
| CN | 1694894 | 11/2005 |
| EP | 0721783 A1 | 7/1996 |
| EP | 0791359 | 8/1997 |
| EP | 811384 A1 | 12/1997 |
| EP | 0931544 A2 | 7/1999 |
| EP | 1 108 435 | 6/2001 |
| EP | 1108435 | 6/2001 |

(Continued)

OTHER PUBLICATIONS

USPTO Non-Final Office Action in U.S. Appl. No. 12/085,065, dated Nov. 26, 2010, 12 pages.

(Continued)

*Primary Examiner* — Xiaozhen Xie
(74) *Attorney, Agent, or Firm* — Fish & Richardson P.C.

(57) ABSTRACT

The present inventors investigated anti-IL-6 receptor antibodies for their effect in suppressing damage to transplanted islets after islet transplantation. As a result, they found that anti-IL-6 receptor antibodies reduced damage to transplanted islets, improved islet survival, and corrected hyperglycemia in recipients. Further, they revealed that administration of the anti-IL-6 receptor antibodies of the present invention suppressed the production of inflammatory cytokines by infiltrating cells after transplantation. Specifically, the present inventors discovered for the first time that damage to transplanted islets after islet transplantation can be suppressed by using anti-IL-6 receptor antibodies according to the present invention.

28 Claims, 10 Drawing Sheets

FOREIGN PATENT DOCUMENTS

| | | |
|---|---|---|
| EP | 1197210 | 4/2002 |
| EP | 1 562 968 | 5/2004 |
| EP | 1 690 550 | 8/2006 |
| EP | 1 707 215 | 10/2006 |
| EP | 1 941 907 | 7/2008 |
| EP | 1 967 207 | 9/2008 |
| EP | 1967209 | 9/2008 |
| EP | 1990060 | 11/2008 |
| EP | 2025346 | 2/2009 |
| ES | 2276525 | 6/2007 |
| FR | 2694767 | 2/1994 |
| JP | 6-237772 | 8/1994 |
| JP | 07-046998 | 2/1995 |
| JP | 08-208514 | 8/1996 |
| JP | 2005-524606 | 8/2005 |
| JP | 2005281235 | 10/2005 |
| JP | 2006524685 | 11/2006 |
| JP | 2007-528691 | 10/2007 |
| JP | 2008-37875 | 2/2008 |
| JP | 2008-37876 | 2/2008 |
| JP | 2008-538931 | 11/2008 |
| RU | 2127117 | 3/1999 |
| RU | 2430111 | 9/2011 |
| WO | WO 92/19759 | 11/1992 |
| WO | WO9420488 A1 | 9/1994 |
| WO | WO 94/28159 | 12/1994 |
| WO | WO 95/09873 | 4/1995 |
| WO | WO 96/25174 | 8/1996 |
| WO | 98/36061 | 8/1998 |
| WO | WO 00/10607 | 3/2000 |
| WO | WO0105394 | 1/2001 |
| WO | WO0145678 | 6/2001 |
| WO | WO03105861 A1 | 12/2003 |
| WO | WO 2004/007701 | 1/2004 |
| WO | WO 2004/039826 * | 5/2004 |
| WO | WO2004045507 | 6/2004 |
| WO | WO2004045512 A2 | 6/2004 |
| WO | WO2004071404 A2 | 8/2004 |
| WO | 2004073741 | 9/2004 |
| WO | WO 2004/096273 * | 11/2004 |
| WO | WO 2005/028514 * | 3/2005 |
| WO | WO 2005/037315 | 4/2005 |
| WO | WO2005044848 A1 | 5/2005 |
| WO | WO 2005/061000 | 7/2005 |
| WO | WO2005107800 A1 | 11/2005 |
| WO | WO 2006/009092 * | 1/2006 |
| WO | WO 2006/070286 | 7/2006 |
| WO | WO 2006/119115 | 11/2006 |
| WO | WO 2007/043641 | 4/2007 |
| WO | WO2007046489 | 4/2007 |
| WO | WO2007058194 | 5/2007 |
| WO | WO2007061029 | 5/2007 |
| WO | WO 2007/076927 | 7/2007 |
| WO | WO2007086490 | 8/2007 |
| WO | WO2007116962 | 10/2007 |
| WO | WO 2008/020079 | 2/2008 |
| WO | 2008090901 | 7/2008 |
| WO | WO 2009/010539 | 1/2009 |
| WO | WO 2009/041613 | 4/2009 |
| WO | WO 2009/041621 | 4/2009 |
| WO | WO 2009/125825 | 10/2009 |
| WO | WO 2009/148148 | 12/2009 |

OTHER PUBLICATIONS

USPTO Restriction Requirement in U.S. Appl. No. 12/161,733, dated Jan. 13, 2011, 7 pages.

Klarquist Sparkman, LLP Response to Restriction Requirement dated Oct. 5, 2010 in U.S. Appl. No. 12/296,193, filed Nov. 2, 2010, 2 pages.

USPTO Non-Final Office Action in U.S. Appl. No. 12/296,193, dated Dec. 20, 2010, 12 pages.

USPTO Restriction Requirement in U.S. Appl. No. 12/094,644, dated Feb. 2, 2011, 5 pages.

Akira et al., "Interleukin-6 in biology and medicine", Advances in Immunology 54:1-78, 1993.

Benda et al., "Interleukin-6 in islet xenograft rejection", Transplant Int. 14:63-71, 2001.

Campbell et al., "Essential role for interferon-γ and interleukin-6 in autoimmune insulin-dependent diabetes in NOD/Wehl mice", J. Clin. Invest. 87:739-742, 1991.

Campbell et al., "Evidence for IL-6 production by and effects on the pancreatic β-cell", J. Immunol. 143:1188-1191, 1989.

Choi et al., "IL-6 protects pancreatic islet beta cells from pro-inflammatory cytokines-induced cell death and functional impairment in vitro and in vivo", Transpl. Immunol. 13:43-53, 2004.

Gwechengerger et al., "Cardiac myocytes produce interleukin-6 in culture and in viable border zone of reperfused infarctions", Circulation 99:546-551, 1999.

Hirano et al., "Complementary DNA for a novel human interleukin (BSF-2) that induces B lymphocytes to produce immunoglobulin", Nature 324:73-76, 1986.

Hirata et al., "Characterization of IL-6 receptor expression by monoclonal and polyclonal antibodies", J. Immunol. 143:2900-2906, 1989.

Huang et al., "A monoclonal anti-human IL-6 receptor antibody inhibits the proliferation of human myeloma cells", Hybridoma 12:621-631, 1993.

Ito et al., Journal of Japan Surgical Society, 5:107 (special extra issue 2):387 (#PS-014-5), 2006. (translation included).

Itoh et al., "Anti-IL-6 receptor antibody down-regulates pro-inflammation cytokine production of Gr-1*CD11b* cells and prevents early loss of islet grafts in the liver of mice in association with engraftments", Transplantation 82(Supp. 3), World Transplant Congress 2006, Abstract No. 2838.

Lotz et al., "B cell stimulating factor 2/interleukin 6 is a costimulant for human thymocytes and T lymphocytes", J. Exp. Med. 167:1253-1258, 1988.

Novick et al., "Monoclonal antibodies to the soluble human IL-6 receptor: affinity purification, ELISA, and inhibition of ligand binding", Hybridoma 10:137-146, 1991.

Taga et al., "Interleukin-6 triggers the association of its receptor with a possible signal transducer, gp130", Cell 58:573-581, 1989.

Taga et al., "Receptors for B cell stimulatory factor 2", J. Exp. Med.166:967-981, 1987.

Yamasaki et al., "Cloning and expression of the human interleukin-6 (BSF-2/IFNβ 2) receptor", Science 241:825-828, 1988.

Yamauchi-Takihara et al., "Hypoxic stress induces cardiac myocyte-derived interleukin-6", Circulation 91:1520-1524, 1995.

Yue et al., "Cytokine expression increases in nonmyocytes from rats with postinfarction heart failure", Am. J. Physiol. 275(1 pt 2):H250-H258, 1998.

Alvarez et al., "Tumor necrosis factor-α exerts interleukin-6-dependent and -independent effects on cultured skeletal muscle cells," *Biochim. Biophys. Acta*, 1542:66-72 (2002).

Barton-Davis et al., "Viral mediated expression of insulin-like growth factor I blocks the aging-related loss of skeletal muscle function," *Proc. Natl. Acad. Sci. USA*, 95:15603-07 (1998).

Bogdanovich et al., "Functional improvement of dystrophic muscle by myostatin blockade," *Nature*, 420:418-421 (2002).

Dangott et al., "Dietary Creatine Monohydrate Supplementation Increases Satellite Cell Mitotic Activity During Compensatory Hypertrophy," *Int. J. Sports Med.*, 21:13-16 (2000).

Darr and Schultz, "Hindlimb suspension suppresses muscle growth and satellite cell proliferation," *J. Appl. Physiol.*, 67:1827-34 (1989).

Ding et al., "The change of plasma interleukin-6 level and cardiac protective effect of monoclonal antibody to IL-6 during myocardial infarction reperfusion," *Chin. J. Cardiol.*, 27:29-32 (1999) (with English Abstract).

Finkel et al., "Negative inotropic effects of cytokines on the heart mediated by nitric oxide," *Science*, 257:387-389 (1992).

Fredj et al., "Role of Interleukin-6 in Cardiomyocyte/Cardiac Fibroblast Interactions During Myocyte Hypertrophy and Fibroblast Proliferation," *J. Cell. Physiol.*, 204:428-436 (2005).

Fuchs et al., "Role of interleukin-6 for LV remodeling and survival after experimental myocardial infarction," *FASEB J.*, 17: 2118-20 (2003).

Garry et al., "Myogenic stem cell function is impaired in mice lacking the *forkhead*/winged helix protein MNF," *Proc. Natl. Acad. Sci. USA*, 97:5416-21 (2000).

Garry et al., "Persistent Expression of MNF Identifies Myogenic Stem Cells in Postnatal Muscles," *Dev. Biol.*, 188:280-294 (1997).

Grossniklaus and Green, "Perspective Choroidal Neovascularization," *Am. J. Ophthalmol.*, 137:496-503 (2004).

Hirota et al., "Continuous activation of gp130, a signal-transducing receptor component for interleukin 6-related cytokines, causes myocardial hypertrophy in mice," *Proc. Natl. Acad. Sci. USA*, 92:4862-66 (1995).

Horinaga et al., "Clinical and Pathologic Significance of Activation of Signal Transducer and Activator of Transcription 3 in Prostate Cancer," *Urology*, 66(3):671-675 (2005).

Jejurikar et al., "Skeletal Muscle Denervation Increases Satellite Cell Susceptibility to Apoptosis," *Plast. Reconstr. Surg.*, 110:160-168 (2002).

Kami et al., "Gene Expression of Receptors for IL-6, LIF, and CNTF in Regenerating Skeletal Muscles," *J. Histochem. Cytochem.*, 48:1203-13 (2000).

Kurek et al., "Up-regulation of leukaemia inhibitory factor and interleukin-6 in transected sciatic nerve and muscle following denervation," *Neuromuscul. Disord.*, 6:105-114 (1996).

Kuroda et al., "Prevention of Cancer Cachexia by a Novel Nuclear Factor κB Inhibitor in Prostate Cancer," *Clin. Cancer Res.*, 11(15):5590-5594 (2005).

Mauro, "Satellite Cell of Skeletal Muscle Fibers," *J. Biophys. Biochem. Cytol.*, 9:493-495 (1961).

McCormick and Schultz, "Role of Satellite Cells in Altering Myosin Expression During Avian Skeletal Muscle Hypertrophy," *Dev. Dyn.*, 199:52-63 (1994).

Moss and Leblond, "Satellite Cells as the Source of Nuclei in Muscles of Growing Rats," *Anat. Rec.*, 170:421-435 (1971).

Mozdziak et al., "Hindlimb suspension reduces muscle regeneration," *Eur. J. Appl. Physiol.*, 78:136-140 (1998).

Mozdziak et al., "Muscle regeneration during hindlimb unloading results in a reduction in muscle size after reloading," *J. Appl. Physiol.*, 91:183-190 (2001).

Mozdziak et al., "Quantitation of Satellite Cell Proliferation in Vivo Using Image Analysis," *Biotech. Histochem.*, 69:249-252 (1994).

Mozdziak et al., "Unloading of juvenile muscle results in a reduced muscle size 9 wk after reloading," *J. Appl. Physiol.*, 88:158-164 (2000).

Murphy, "The effect of mechanical stretch on proliferation and differentiation of C2C12 cells," *FASEB J.*, 18:A743 (Abstract #476.6) (2004).

Nagai et al., Ensho-Saisei (Inflammation and Regeneration), Jul. 2006; 26(4):367 (#90) (English translation included).

Nakashima et al., "Serum Interleukin 6 as a Prognostic Factor in Patients with Prostate Cancer," *Clin. Cancer Res.*, 6(7):2702-2706 (2000).

Negoro et al., "Activation of JAK/STAT pathway transduces cytoprotective signal in rat acute myocardial infarction," *Cardiovas. Res.*, 47:797-805 (2000).

Nishimoto and Kishimoto, "Inhibition of IL-6 for the treatment of inflammatory diseases," *Curr. Opin. Pharmacol.*, 4:386-391 (2004).

Okamoto et al., "Interleukin-6 as a Paracrine and Autocrine Growth Factor in Human Prostatic Carcinoma Cells in Vitro," *Cancer Res.*, 57:141-146 (1997).

Okazaki et al., "Characterization of anti-mouse interleukin-6 receptor antibody," *Immunol. Lett.*, 84:231-240 (2002).

Ono et al., "Cytokine gene expression after myocardial infarction in rat hearts," *Circulation*, 98:149-156 (1998).

Pauleikhoff, "Neovascular Age-Related Macular Degeneration," *Retina*, 25:1065-84 (2005).

Schultz et al., "Response of satellite cells to focal skeletal muscle injury," *Muscle Nerve*, 8:217-222 (1985).

Schultz, "Acute effects of hindlimb unweighting on satellite cells of growing skeletal muscle," *J. Appl. Physiol.*, 76:266-270 (1994).

Schultz, "Satellite Cell Proliferative Compartments in Growing Skeletal Muscles," *Dev. Biol.*, 175:84-94 (1996).

Seddon et al., "Progression of Age-Related Macular Degeneration," *Arch. Ophthalmol.*, 123:774-782 (2005).

Shimazaki et al., "Hito Kotsuzuishu Model to Ko hito IL-6 Juyotai Kotai no Ko Shuyo Koka," *Rinsho Ketsueki*, 38:281-284 (1997) (English translation provided).

Smith et al., "Anti-Interleukin-6 Monoclonal Antibody Induces Regression of Human Prostate Cancer Xenografts in Nude Mice," *Prostate*, 48:47-53 (2001).

Snow, "Myogenic Cell Formation in Regenerating Rat Skeletal Muscle Injured by Mincing," *Anat. Rec.*, 188:181-199 (1977).

Snow, "Satellite Cell Response in Rat Soleus Muscle Undergoing Hypertrophy Due to Surgical Ablation of Synergists," *Anat. Rec.*, 227:437-446 (1990).

Tsujinaka et al., "Interleukin 6 Receptor Antibody Inhibits Muscle Atrophy and Modulates Proteolytic Systems in Interleukin 6 Transgenic Mice," *J. Clin. Invest.*, 97:244-249 (1996).

Wang et al., "Mechanical load-dependent regulation of satellite cell and fiber size in rat soleus muscle," *Am. J. Physiol. Cell. Physiol.*, 290:C981-C989 (2006).

Warren et al., "Physiological role of tumor necrosis factor I in traumatic muscle injury," *FASEB J.*, 16:1630-32 (2002).

Yamasaki et al., "Cloning and Expression of the Human Interleukin-6 (BSF-2/IFNβ 2) Receptor," *Science*, 241:825-828 (1988).

Zaki et al., "CNTO 328, a Monoclonal Antibody to IL-6, Inhibits Human Tumor-Induced Cachexia in Nude Mice," *Int. J. Cancer*, 111:592-595 (2004).

International Preliminary Report on Patentability for App. Ser. No. PCT/JP2006/320905, dated Apr. 22, 2008, 8 pages.

Japanese Patent Office, International Search Report for App. Ser. No. PCT/JP2006/320905, mailed Jan. 16, 2007, 2 pages.

International Preliminary Report on Patentability for App Ser. No. PCT/JP2006/322726, dated May 20, 2008, 9 pages.

Japanese Patent Office, International Search Report for App. Ser. No. PCT/JP2006/322726, mailed Jan. 19, 2007, 5 pages.

International Preliminary Report on Patentability for App. Ser. No. PCT/JP2006/323392, dated May 27, 2008, 9 pages.

Japanese Patent Office, International Search Report for App. Ser. No. PCT/JP2006/323392, mailed Jan. 9, 2007, 4 pages.

International Preliminary Report on Patentability for App. Ser. No. PCT/JP2007/051226, dated Jul. 29, 2008, 6 pages.

Japanese Patent Office, International Search Report for App. Ser. No. PCT/JP2007/051226, mailed May 1, 2007, 2 pages.

International Preliminary Report on Patentability for App. Ser. No. PCT/JP2007/057745, dated Nov. 17, 2008, 6 pages.

Japanese Patent Office, International Search Report for App. Ser. No. PCT/JP2007/057745, mailed Jul. 10, 2007, 2 pages.

International Preliminary Report on Patentability for App. Ser. No. PCT/JP2006/320441, dated Apr. 16, 2008, 5 pages.

Japanese Patent Office, International Search Report for App. Ser. No. PCT/JP2006/320441, mailed Dec. 19, 2006, 2 pages.

Borsellino et al., "Blocking signaling through the Gp130 receptor chain by interleukin-6 and oncostatin M inhibits PC-3 cell growth and sensitizes the tumor cells to etoposide and cisplatin-mediated cytotoxicity," Cancer, 85(1):134-44 (1999).

Culig et al., "Interleukin-6 regulates androgen receptor activity and prostate cancer cell growth," Mol. Cell. Endocrinol., 197(1-2):231-238 (2002).

Davies et al, "The HGF/SF antagonist NK4 reverses fibroblast- and HGF-induced prostate tumor growth and angiogenesis in vivo," Int. J. Cancer, 106(3):348-354 (2003).

Eder et al., "Targeting the androgen receptor in hormone-refractory prostate cancer—new concepts," Future Oncol., 1(1):93-101 (2005).

Lee et al., "Interleukin-6 protects LNCaP cells from apoptosis induced by androgen deprivation through the Stat3 pathway," Prostate, 60(3):178-186 (2004).

Paule, "Reappraisal of the concept of hormone therapy in metastatic prostate cancer and implications for treatment," Eur. Urol., 47(6):729-735 (2005).

Trikha et al., "Targeted anti-interleukin-6 monoclonal antibody therapy for cancer: a review of the rationale and clinical evidence," Clin. Cancer Res., 9(13):4653-4665 (2003).

Xing et al., "The effect of interleukin-6 on the proliferation of prostate cancer cells in vitro and the modulation of this procedure," J. Tongji Med. Univ., 21(3):225-227 (2001).

European Search Report for App. Ser. No. 06 83 3196, dated Aug. 27, 2009, 5 pages.

Jeron et al., "Systemic Immunosuppression Fails to Suppress Cardiac Cytokine induction in Pressure Overload Hypertrophy in Rats," Immunobiology, 205(1):51-60 (2002).

Kobara et al., "Inhibition of interleukin-6 signaling attenuates left ventricular remodeling after myocardial infarction in mice," Journal of the American Heart Association, 112(17):851 (2005).

Kurdi et al., "Increased expression of IL-6 and LIF in the hypertrophied left ventricle of TGR(mRen2)27 and SHR rats," Molecular and Cellular Biochemistry, 269(1):95-101 (2005).

Okamoto et al., "Inhibition of Interleukin-6 Signaling Attenuates Left Ventricular Remodeling After Experimental Myocardial Infarction," Journal of Cardiac Failure, 11(9): P066 (2005).

European Search Report for App. Ser. No. EP 06 81 2073, dated Nov. 20, 2009, 6 pages.

Ford et al., "Evidence that Production of Interleukin 6 within the Rejecting Allograft Coincides with Cytotoxic T Lymphocyte Development," Transplantation, 51(3):656-661 (1991).

Luo et al., "A Proteasome Inhibitor Effectively Prevents Mouse Heart Allograft Rejection," Transplantation, 72(2):196-202 (2001).

European Search Report for App. Ser. No. EP 06 83 2657, dated Nov. 25, 2009, 5 pages.

Biswas et al., "Involvement of IL-6 in the paracrine production of VEGF in ocular HSV-1 infection," Exp. Eye Res., 82(1):46-54 (2006).

Giugliano et al., "Verapamil inhibits interleukin-6 and vascular endothelial growth factor production in primary cultures of keloid fibroblasts," Br. J. Plast. Surg., 56(8):804-809 (2003).

Hoffman et al., "Inhibitory effects of verapamil isomers on the proliferation of choroidal endothelial cells," Graefe's Arch. Clin. Exp. Ophthalmol., 244(3):376-381 (2006).

Park et al., "Interleukin-6 protects MIN6 beta cells from cytokine-induced apoptosis," Ann. N.Y. Acad. Sci., 1005:242-249 (2003).

USPTO Restriction Requirement in U.S. Appl. No. 12/090,676, dated Mar. 12, 2010, 4 pages.

European Search Report for App. Ser. No. 07 70 7458, dated Nov. 30, 2009, 5 pages.

European Search Report for App. Ser. No. EP 06 81 1729, dated Nov. 17, 2009, 5 pages.

Quentmeier et al., "Role of IL-6, IL-2, and IL-4 in the in Vitro Induction of Cytotoxic T Cells," J. Immunol., 149(10):3316-3320 (1992).

USPTO Restriction Requirement in U.S. Appl. No. 12/085,065, dated Apr. 30, 2010, 8 pages.

Furukawa et al., "Cytokine gene expression during the development of graft coronary artery disease in mice," Jpn.Cir. J., 63:775-782 (1999).

Hornick et al., "Chronic rejection in the heart," Methods Mol. Biol., 333:131-144 (2006).

Izawa et al., "Critical Role of Interleukin-6 and its Crosstalk with AT1R Signaling in Acute Rejection of Murine Cardiac Allografts," Circulation Journal, 71 (Suppl. 1):392 (#PE-269), Annual Scientific Meeting of the Japanese Circulation Society, Kobe, Japan (2007).

Izawa et al., "Interleukin-6 Blockade Attenuates the Development of Both Acute and Chronic Rejection of Murine Cardiac Allografts: A Potential Crosstalk between Interleukin-6 and Signaling through Angiotensin II Type 1 Receptor," American Journal of Transplantation, 7 (Suppl. 11):426 (#1084), American Transplant Congress, San Francisco, CA (2007).

Kurek et al., "The Role of Leukemia Inhibitory Factor in Skeletal Muscle Regeneration," Muscle Nerve, 20:815-822 (1997).

Ramzy et al., "Cardiac allograft vasculopathy: a review," Can. J. Surg., 48:319-327 (2005).

Valantine, "Cardiac allograft vasculopathy after heart transplantation: risk factors and management," J. Heart Lung Transplant., 23(5 Suppl.):S187-S193 (2004).

Webber et al., "Heart and lung transplantation in children," Lancet, 368:53-69 (2006).

Wong et al., "Progress in heart transplantation," Cardiovasc. Pathol., 14:176-180 (2005).

International Search Report for App. Ser. No. PCT/JP2008/050842, mailed on Feb. 19, 2008, 2 pages.

Bellomo, "The Cytokine Network in the Critically Ill," Anaesth. Intensive Care, 20(3):288-302 (1992).

Shimizu et al., "Cancer anti-angiogenic therapy," Biol. Pharm. Bull., 27(5):599-605 (2004).

Stan et al., "In vivo inhibition of angiogenesis and growth of the human U-87 malignant glial tumor by treatment with an antibody against basic fibroblast growth factor," J. Neurosurg., 82(6):1044-52 (1995).

Tobe et al., "Targeted disruption of the FGF2 gene does not prevent choroidal neovascularization in a murine model," Am. J. Pathol., 153(5):1641-6 (1998).

Fish & Richardson P.C., Response to Restriction Requirement dated Mar. 12, 2010 in U.S. Appl. No. 12/090,676, filed Aug. 31, 2010, 1 page.

Guice et al., "Anti-tumor necrosis factor antibody augments edema formation in caerulein-induced acute pancreatitis," J. Surg. Res., 51(6):495-9 (1991).

Hocking et al., "Mechanisms of pulmonary edema induced by tumor necrosis factor-alpha," Circ. Res., 67(1):68-77 (1990).

Knulst et al., "Cytokine detection and modulation in acute graft vs. host disease in mice," Mediators Inflamm., 3(1):33-40 (1994).

Mukaida et al., "Cytokines and immune network," Rinsho Kensa, 35(5):447-452, Japan (1991).

Murata et al., The Saishin-nigaku, 47(11):49-56 (1992).

Ulich et al., "Intratracheal injection of endotoxin and cytokines. II. Interleukin-6 and transforming growth factor beta inhibit acute inflammation," Am. J. Pathol., 138(5):1097-1101 (1991).

Bork, "Powers and pitfalls in sequence analysis: the 70% hurdle," Genome Res., 10:398-400 (2000).

Brenner, "Errors in genome annotation," Trends Genet., 15(4):132-133 (1999).

Doerks et al., "Protein annotation: detective work for function prediction," Trends Genet., 14(6):248-250 (1998).

Kobara et al., "Antibody against interleukin-6 receptor attenuates left ventricular remodelling after myocardial infarction in mice," Cardiovasc. Res., 87:424-430 (2010).

Matsushita et al., "Interleukin-6/soluble interleukin-6 receptor complex reduces infarct size via inhibiting myocardial apoptosis," Lab. Invest, 85:1210-1223 (2005).

Ngo et al., "The Protein Folding Problem and Tertiary Structure Prediction, Chapter 14: Computational Complexity Protein Structure Prediction, and the Levinthal Paradox," 433-440 and 492-495 (1994).

Phillips, "The challenge of gene therapy and DNA delivery," J. Pharm. Pharmacol., 53:1169-1174 (2001).

Pirollo et al., "Targeted delivery of small interfering RNA: approaching effective cancer therapies," Cancer Res., 68(5):1247-1250 (2008).

Skolnick et al., "From genes to protein structure and function: novel applications of computational approaches in the genomic era," Trends Biotechnol., 18(1):34-39 (2000).

Vidal et al., "Making sense of antisense," Eur. J. Cancer, 41:2812-2818 (2005).

Wells, "Additivity of mutational effects in proteins," Biochemistry, 29(37):8509-8517 (1990).

USPTO Non-Final Office Action in U.S. Appl. No. 12/090,676, dated Oct. 6, 2010, 18 pages.

USPTO Restriction Requirement in U.S. Appl. No. 12/296,193, dated Oct. 5, 2010, 6 pages.

Smith et al., "The challenges of genome sequence annotation or 'The devil is in the details,'" Nat. Biotechnol., 15:1222-1223 (1997).

Fish & Richardson P.C., Response to Restriction Requirement dated Apr. 30, 2010 in U.S. Appl. No. 12/085,065, filed Oct. 22, 2010, 2 pages.

Fisniku et al., "Protective effects of PG490-88 on chronic allograft rejection by changing intragraft gene expression profiles," Transplant Proc., 37:1962-1964 (2005).

Kallen et al., "New developments in IL-6 dependent biology and therapy: where do we stand and what are the options?," Expert Opin. Investig. Drugs, 8(9):1327-49 (1999).

Matsuda et al., "Establishment of an interleukin 6 (IL 6)/B cell stimulatory factor 2-dependent cell line and preparation of anti-IL 6 monoclonal antibodies," Eur. J. Immunol., 18:951-956 (1988).

Shimizu et al., "KRP-203, a novel synthetic immunosuppressant, prolongs graft survival and attenuates chronic rejection in rat skin and heart allografts," Circulation, 111:222-229 (2005).

Tamura et al., "Soluble interleukin-6 receptor triggers osteoclast formation by interleukin 6," Proc. Natl. Acad. Sci. U.S.A., 90:11924-11928 (1993).

Campo et al., "Comparative activity of Sant7 and anti-IL-6, IL-6R monoclonal antibodies in a murine model of B-cell lymphoma," *Cytokine*, 31(5):368-74 (2005).

Idezawa et al., "Interleukin-6 Functions as an Autocrine Invasion Factor of Human Pancreatic Cancer Cells," *Yamanashi Med. J.*, 19(2):53-67 (2004).

Idezawa et al., "Interleukin-6 Functions as an Autocrine Invasion Factor of Human Pancreatic Cancer Cells," *Yamanashi Med. J.*, 20(2):xxxvi (2005).

Kamohara et al., "IL-6 no Suigan Saibo no Zoshoku-Ten'i Oyobosu Eikyo to Kanshitsu Saibo ni yoru Hatsugen Seigyo Kiko," *Japanese Journal of Gastroenterological Surgery*, 39(7):1356 (Abstract 2529) (2006).

Patel et al., "Endogenous interleukin-6 enhances the renal injury, dysfunction, and inflammation caused by ischemia/reperfusion," *J. Pharmacol. Exp. Ther.*, 312(3):1170-1178 (2005).

Paul, W.E. (Ed.), Fundamental Immunology, 3$^{rd}$ ed., New York: Raven Press, 1993, p. 1124-1125.

Skurkovich et al., "Anticytokine therapy—new approach to the treatment of autoimmune and cytokine-disturbance diseases," *Med. Hypotheses*, 59(6):770-780 (2002) (In the Russian language. Relevant portions are in the English language).

Tisdale, MJ., "Biology of cachexia," *J. Natl. Cancer Inst.*, 89(23):1763-73 (1997).

Wilansky, "Echocardiography in the Assessment of Complications of Myocardial Infarction," *Texas Heart Institute Journal*, 18:237-242 (1991).

USPTO Final Office Action in U.S. Appl. No. 12/090,676, dated Jun. 8, 2011, 14 pages.

Fish & Richardson P.C., Amendment in Reply to Action dated Oct. 6, 2010, in U.S. Appl. No. 12/090,676, filed Apr. 5, 2011, 12 pages.

Fish & Richardson P.C., Amendment in Reply to Action dated Nov. 26, 2011 in U.S. Appl. No. 12/085,065, filed May 25, 2011, 9 pages.

USPTO Notice of Allowance in U.S. Appl. No. 12/085,065, dated Aug. 22, 2011, 8 pages.

Klarquist Sparkman, LLP, Amendment and Reply to Office Action dated Dec. 20, 2010 in U.S. Appl. No. 12/296,193, filed Jun. 20, 2011, 24 pages.

USPTO Final Office Action in U.S. Appl. No. 12/296,193, dated Jul. 26, 2011, 20 pages.

Fish & Richardson P.C., Response to Restriction Requirement dated Jan. 13, 2011 in U.S. Appl. No. 12/161,733, filed Jul. 7, 2011, 1 page.

USPTO Non-Final Office Action in U.S. Appl. No. 12/161,733, dated Aug. 16, 2011, 20 pages.

Fish & Richardson P.C., Response to Species Election Requirement dated Feb. 2, 2011 in U.S. Appl. No. 12/094,644, filed Jul. 25, 2011, 2 pages.

USPTO Non-Final Office Action in U.S. Appl. No. 12/094,644, dated Sep. 26, 2011, 6 pages.

European Search Report for App. Ser. No. 07 741 181.7, mailed Dec. 23, 2009, 6 pages.

International Search Report for App. Ser. No. PCT/JP2009/060314, mailed Aug. 11, 2009, 7 pages.

International Preliminary Report on Patentability for App. Ser. No. PCT/JP2009/060314, mailed Jan. 11, 2011, 8 pages.

European Search Report for App. Ser. No. 08 703 686.9, mailed Aug. 24, 2010, 12 pages.

USPTO Non-Final Office Action in U.S. Appl. No. 12/524,041, dated Aug. 29, 2011, 6 pages.

Sterne, Kessler, Goldstein & Fox P.L.L.C, Amendment and Reply to Office Action dated Aug. 29, 2011 in U.S. Appl. No. 12/524,041, filed Jun. 20, 2012, 7 pages.

Guillén et al., "Cytokine signaling during myocardial infarction: sequential appearance of IL-1 beta and IL-6," *Am. J. Physiol.*, 269(2 Pt 2):R229-35 (1995).

USPTO Restriction Requirement in U.S. Appl. No. 12/524,041, dated Aug. 29, 2011, 6 pages.

Sterne, Kessler, Goldstein & Fox P.L.L.C., Response to Restriction Requirement dated Aug. 29, 2011 in U.S. Appl. No. 12/524,041, filed Oct. 28, 2011, 2 pages.

USPTO Non-Final Office Action in U.S. Appl. No. 12/524,041, dated Dec. 21, 2011, 7 pages.

Nishimoto et al., "Anti-interleukin 6 receptor antibody treatment in rheumatic disease," *Ann Rheum. Dis.* 59 Suppl 1:i21-27 (2000).

Fujita et al., "Anti-interleukin-6 receptor antibody prevents muscle atrophy in colon-26 adenocarcinoma-bearing mice with modulation of lysosomal and ATP-ubiquitin-dependent proteolytic pathways," *Int. J. Cancer*, 68(5):637-643 (1996).

Ohtsuka et al., "Relation of circulating interleukin-6 to left ventricular remodeling in patients with reperfused anterior myocardial infarction," *Clin. Cardiol.*, 27(7):417-420 (2004).

Q&A de wakaru himan to tounyoubyou, 3(6):982-984 (2004) (with English translation).

Fish & Richardson P.C., Amendment and Reply to Action dated Sep. 26, 2011 in U.S. Appl. No. 12/094,644, filed Mar. 21, 2012, 9 pages.

Ashizawa et al., "Clinical significance of interleukin-6 (IL-6) in the spread of gastric cancer: role of IL-6 as a prognostic factor," *Gastric Cancer*, 8:124-131 (2005).

Bond et al., "Synergistic upregulation of metalloproteinase-9 by growth factors and inflammatory cytokines: an absolute requirement for transcription factor NF-kappa B," *FEBS Lett.*, 435:29-34 (1998).

Gao et al., "Mutations in the EGFR kinase domain mediate STAT3 activation via IL-6 production in human lung adenocarcinomas," *J. Clin. Invest.*, 117(12):3846-3856 (2007).

Ghosh et al., "Missing pieces in the NF-kappaB puzzle," Cell, 109:S81-S96 (2002).

Greten et al., "IKKbeta links inflammation and tumorigenesis in a mouse model of colitis-associated cancer," *Cell*, 118:285-296 (2004).

Karin et al., "NF-kappaB at the crossroads of life and death," *Nat. Immunol.*, 3(3):221-227 (2002).

Karin et al., "NF-kappaB in cancer: from innocent bystander to major culprit," *Nat. Rev. Cancer*, 2:301-310 (2002).

Maeda et al., "IKKbeta couples hepatocyte death to cytokine-driven compensatory proliferation that promotes chemical hepatocarcinogenesis," *Cell*, 121:977-990 (2005).

Maeda et al., "Ikappa B kinasebeta/nuclear factor-kappaB activation controls the development of liver metastasis by way of interleukin-6 expression," *Hepatology*, 50:1851-1860 (2009).

Matzaraki et al., "Evaluation of serum procalcitonin and interleukin-6 levels as markers of liver metastasis," *Clin. Biochem.*, 40:336-342 (2007).

Naugler et al., "Gender disparity in liver cancer due to sex differences in MyD88-dependent IL-6 production," *Science*, 317:121-124 (2007).

Pikarsky et al., "NF-kappaB functions as a tumour promoter in inflammation-associated cancer," *Nature*, 431:461-466 (2004).

Sansone et al., "IL-6 triggers malignant features in mammospheres from human ductal breast carcinoma and normal mammary gland," *J. Clin. Invest.*, 117(12):3988-4002 (2007).

Sarkar et al., "Back to the future: COX-2 inhibitors for chemoprevention and cancer therapy," *Mini Rev. Med. Chem.*, 7:599-608 (2007).

Steeg et al., "Tumor metastasis: mechanistic insights and clinical challenges," *Nat. Med.*, 12(8):895-904 (2006).

Steeg, "Metastasis: a therapeutic target for cancer," *Nat. Clin. Pract. Oncol.*, 5(4):206-219 (2008).

Studebaker et al., "Fibroblasts isolated from common sites of breast cancer metastasis enhance cancer cell growth rates and invasiveness in an interleukin-6-dependent manner," *Cancer Res.*, 68(21):9087-9095 (2008).

Takeda et al., "Murine tumor cells metastasizing selectively in the liver: ability to produce hepatocyte-activating cytokines interleukin-1 and/or -6," *Jpn. J. Cancer Res.*, 82:1299-1308 (1991).

Yamakawa et al., "Astrocytes promote the proliferation of lung cancer cells in brain metastases via inflammatory cytokines, especially IL-6," *Neuroscience*, 48(2/3):216, P-22 (poster presentation) (2009).

International Search Report for App. Ser. No. PCT/JP2010/062874, mailed Aug. 31, 2010, 2 pages.

Fish & Richardson P.C., Amendment in Reply to Action dated Jun. 8, 2012, in U.S. Appl. No. 12/090,676, filed Jun. 29, 2012, 13 pages.

Sterne, Kessler, Goldstein & Fox P.L.L.C., Amendment and Reply to Office Action dated Aug. 9, 2011 in U.S. Appl. No. 12/524,041, filed Jun. 20, 2012, 7 pages.

USPTO Non-Final Office Action in U.S. Appl. No. 12/996,162, dated Jun. 1, 2012, 8 pages.
International Preliminary Report on Patentability for App. Ser. No. PCT/JP2010/062874, mailed Feb. 7, 2012, 9 pages.
Campochiaro, "Retinal and choroidal neovascularization," *J. Cell Physiol.*, 184:301-310 (2000).
Chuntharapai et al., "Generation of monoclonal antibodies to chemokine receptors," *Methods Enzymol.*, 288:15-27 (1997).
Fujita et al., "Anti-interleukin-6 receptor antibody prevents muscle atrophy in colon-26 adenocarincoma-bearing mice with modulation of lysosomal and ATP-ubiquitin-dependent proteolytic pathways," *Int. J. Cancer*, 68(5):637-643 (1996).
Greenberg et al., "Interleukin 6 reduces lipoprotein lipase activity in adipose tissue of mice in vivo and in 3T3-L1 adipocytes: a possible role for interleukin 6 in cancer cachexia," *Cancer Res.*, 52(15):4113-4116 (1992).
Ohtsuka et al., "Relation of circulating interleukin-6 to left ventricular remodeling in patients with reperfused anterior myocardial infarction," *Clin. Cardiol.*, 27(7): 417-420 (2004).
Ono et al., "The effect of IL-6 on the des-gamma-carboxy prothrombin synthesis in human hepatoma cells," *Gastroenterologia Japonica*, 27(6):745-50 (1992).
Puhakka et al., "Interleukin-6 and tumor necrosis factor alpha in relation to myocardial infarct size and collagen formation," *J. Card. Fail.*, 9(4):325-332 (2003).
Q&A de wakarn human to tounyoubyou, 3(6):982-684 (2004) (with English translation).
Sato et al., "Reshaping a human antibody to inhibit the interleukin 6-dependent tumor cell growth," *Cancer*, 53:851-856 (1993).
Strassmann et al., "Evidence for the involvement of interleukin 6 in experimental cancer cachexia," *J. Clin. Invest.*, 89(5):1681-1684 (1992).
USPTO Notice of Allowance in U.S. Appl. No. 12/085,065, dated Jan. 11, 2012, 7 pages.
Fish & Richardson P.C., Amendment and Reply to Office Action dated Aug. 16, 2011 in U.S. Appl. No. 12/161,733, filed Feb. 15, 2012, 13 pages.
Klarquist Sparkman, LLP, Amendment and Reply to Office Action dated Jul. 26, 2011 in U.S. Appl. No. 12/296,193, filed Jan. 26, 2012, 10 pages.
Klarquist Sparkman, LLP, Supplemental Amendment and Response in U.S. Appl. No. 12/296,193, filed Mar. 19, 2012, 6 pages.
Fish & Richardson P.C., Amendment and Reply to Action dated Sep. 26, 2011 in U.S. Appl. No. 12/094,644, fild Mar. 21, 2012, 9 pages.
USPTO Final Office Action in U.S. Appl. No. 12/161,733, dated Apr. 9, 2012, 20 pages.
USPTO Non-Final Office Action in U.S. Appl. No. 12/085,065, dated Apr. 11, 2012, 8 pages.
USPTO Non-Final Office Action in U.S. Appl. No. 12/094,644, dated May 22, 2012, 10 pages.
USPTO Non-Final Office Action in U.S. Appl. No. 12/085,065, dated Jan. 11, 2013, 14 pages.
Hirai et al., "Perineural invasion in pancreatic cancer," *Pancreas*, 24(1):15-25 (2002).
Martignoni et al., "Role of mononuclear cells and inflammatory cytokines in pancreatic cancer-related cachexia," *Clin. Cancer Res.*, 11(16):5802-5808 (2005).
Miyamoto et al., "Interleukin-6 inhibits radiation induced apoptosis in pancreatic cancer cells," *Anticancer Res.*, 21:2449-2456 (2001).
Okada et al., "Experimental implication of celiac ganglionotropic invasion of pancreatic-cancer cells bearing c-ret proto-oncogene with reference to glial-cell-line-derived neurotrophic factor (GDNF)," *Int. J. Cancer*, 81:67-73 (1999).
Takahashi et al., "Antiproteases in preventing the invasive potential of pancreatic cancer cells," *JOP*, 8(4 Suppl.):501-508 (2007).
Sterne, Kessler, Goldstein & Fox P.L.L.C, Response to Restriction Requirement dated Jun. 1, 2012 in U.S. Appl. No. 12/996,162, filed Jun. 28, 2012, 4 pages.
USPTO Non-Final Office Action in U.S. Appl. No. 12/996,162, dated Sep. 12, 2012, 8 pages.
Nishimoto et al., "Clinical studies in patients with Castleman's disease, Crohn's disease, and rheumatoid arthritis in Japan," *Clin. Rev. Allergy Immunol.*, 28(3):221-30 (2005).
Roitt et al., *Immunology, M. Mir*, p. 110 (2000) (with English translation).
Yokota et al., "Clinical study of tocilizumab in children with systemic-onset juvenile idiopathic arthritis," *Clin. Rev. Allergy Immunol.*, 28(3):231-8 (2005).
Hirota et al., "Loss of a gp130 cardiac muscle cell survival pathway is a critical event in the onset of heart failure during biomechanical stress," *Cell* 97(2):189-98 (1999).
U.S. Appl. No. 13/700,355, filed Nov. 27, 2012, Nishimura.
USPTO Final Office Action in U.S. Appl. No. 12/524,041, dated Oct. 15, 2012, 6 pages.
Sterne, Kessler, Goldstein & Fox P.L.L.C, Amendment and Reply to Office Action dated Oct. 15, 2012 in U.S. Appl. No. 12/524,041, filed Jan. 15, 2013, 7 pages.
Ceyhan et al., "Neural invasion in pancreatic cancer: a mutual tropism between neurons and cancer cells," *Biochem. Biophys. Res. Commun.*, 374:442-447 (2008).
Maeda et al., "Essential Roles of IKKbeta/NF-κB Activation for Development of Liver Metastasis in Mice," *Gastroenterol*, 130:P-1-P-350, Supplement 2, AASLD Abstracts, p. A-750, abstract No. 107, Elsevier Inc. (2006).
Maeda et al., "Role of IKKbeta/NF-κB Activation for Development of Liver Metastasis," Supplement: The 58th Annual Meeting of the American Association for the Study of Liver Diseases, *Hepatol.*, 46: Issue Supplement S1, AASLD Abstracts, p. 518A, abstract No. 630, American Association for the Study of Liver Diseases (2007).
Beck et al., "Brief report: alleviation of systemic manifestations of Castleman's disease by monoclonal anti-interleukin-6 antibody," *N. Engl. J. Med.*, 330:602-605 (1994).
Choy et al., "Inhibiting interleukin-6 in rheumatoid arthritis," *Curr. Rheumatol. Rep.*, 10(5):413-7 (2008).
Ewert et al., "Stability improvement of antibodies for extracellular and intracellular applications: CDR grafting to stable frameworks and structure-based framework engineering," *Methods*, 34:184-199 (2004).
Guerne et al., "Synovium as a source of interleukin 6 in vitro. Contribution to local and systemic manifestations of arthritis," *J. Clin. Invest.*, 83(2):585-92 (1989).
Hanes et al., "Picomolar affinity antibodies from a fully synthetic naive library selected and evolved by ribosome display," *Nat. Biotechnol.*, 18(12):1287-92 (2000).
Hirano et al., "Excessive production of interleukin 6/B cell stimulatory factor-2 in rheumatoid arthritis," *Eur. J Immunol.*, 18(11):1797-801 (1988).
Houssiau et al., "Interleukin-6 in synovial fluid and serum of patients with rheumatoid arthritis and other inflammatory arthritides," *Arthritis Rheum.*, 31(6):784-8 (1988).
Kishimoto, "The biology of interleukin-6," *Blood*, 74(1):1-10 (1989).
Kotake et al., "Interleukin-6 and soluble interleukin-6 receptors in the synovial fluids from rheumatoid arthritis patients are responsible for osteoclast-like cell formation," *J. Bone Miner Res.*, 11(1):88-95 (1996).
Madhok et al., "Serum interleukin 6 levels in rheumatoid arthritis: correlations with clinical and laboratory indices of disease activity," *Ann. Rheum. Dis.*, 52(3):232-4 (1993).
Nishimoto et al., "Interleukin 6: from bench to bedside," *Nat. Clin. Pract. Rheumatol.*, 2(11):619-26 (2006).
Sack et al., "Interleukin-6 in synovial fluid is closely associated with chronic synovitis in rheumatoid arthritis," *Rheumatol. Int.*, 13(2):45-51 (1993).
Fish & Richardson P.C., Amendment in Reply to Action dated Apr. 11, 2012 in U.S. Appl. No. 12/085,065, filed Oct. 9, 2012, 10 pages.
Fish & Richardson P.C., Amendment and Reply to Office Action dated Apr. 9, 2012 in U.S. Appl. No. 12/161,733, filed Oct. 9, 2012, 13 pages.

* cited by examiner

US 8,470,316 B2

AGENTS FOR SUPPRESSING DAMAGE TO TRANSPLANTED ISLETS AFTER ISLET TRANSPLANTATION

CROSS-REFERENCE TO RELATED APPLICATIONS

This application is the National Stage of International Application Serial No. PCT/JP2006/320441, filed on Oct. 13, 2006, which claims the benefit of Japanese Application Serial No. 2005-300489, filed on Oct. 14, 2005. The contents of both of the foregoing applications are hereby incorporated by reference in their entirety.

TECHNICAL FIELD

The present invention relates to agents for suppressing damage to transplanted islets after islet transplantation, which comprise IL-6 inhibitors as active ingredients, and to uses thereof.

BACKGROUND ART

Insulin is a hypoglycemic hormone. Insulin dependent diabetes is caused by selective destruction of insulin-producing cells (islet β-cells) through immunological mechanisms, and its onset is known to result in hyperglycemia, which causes various disorders. In conventional therapy, preparations of the undersupplied insulin are administered (injected) to compensate for the shortage of insulin to redress hyperglycemia. However, strict blood sugar control is difficult in insulin-based therapies, which can lead to over-administration that can cause fatal hypoglycemia. After the onset of diabetes, diabetic vascular complications progress (such as retinopathy, nephropathy, and neuropathy). Conventional therapeutic methods such as insulin injections cannot halt this progress, leading to therapeutically serious problems. Blood sugar is physiologically controlled chiefly by the regulatory mechanism of islet β-cells; however, in insulin dependent diabetes, the deletion of these islets results in violent ups and downs in blood sugar level, causing the above-described clinical symptoms.

In recent years, Europe and the United States have started clinical application of islet transplantation, where pancreatic islets of Langerhans (islets) are transplanted as a means for treating diabetes. This attempts treatment not by administering insulin, but by transplanting insulin-producing cells. The practical procedure of clinical islet transplantation is as follows: ultrasound-guided percutaneous, transpulmonary portal vein catheterization is carried out under local anesthesia; and then donor islets are transplanted to the liver via the catheter. The islet grafts survive at the end of the portal vein, and control blood sugar level by secreting insulin. When successful, islet transplantation restores normal blood sugar to diabetic recipients, such that insulin treatment becomes unnecessary. To date, however, successful cases of clinical islet transplantation are limited. Further, transplantation to a single recipient requires islets isolated from the pancreas of two or three donors. Specifically, since islet function disorders that appear immediately after transplantation reduce graft viability, islet transplantation from a single donor to a single recipient is insufficient, and thus, transplantation from two to three donors to a single recipient is carried out. Some reports suggest only 20% to 30% of transplanted grafts survive. Details of these functional disorders remain unclear, but they pose an extremely serious problem in terms of improving the results of clinical islet transplantation.

Conventionally, islet transplantation has been performed using islets isolated from the pancreases of brain-dead donors or donors under cardiac arrest. Recent reports also describe successful cases of living donor islet transplantation, in which islets are isolated and purified from a portion of pancreas excised from healthy donors and transplanted to diabetic patients. Such living donor islet transplantation is invasive and a burden for donors. Thus, it is preferable to enable treatments that suppress damage to transplanted islets just after transplantation and that use fewer donor islets.

IL-6 is a cytokine called B-cell stimulating factor 2 (BSF2) or interferon β2. IL-6 was discovered as a differentiation factor involved in the activation of B-cell lymphocytes (Non-patent Document 1), and was later revealed to be a multifunctional cytokine that influences the function of various cells (Non-patent Document 2). IL-6 has been reported to induce maturation of T lymphocyte cells (Non-patent Document 3).

IL-6 transmits its biological activity via two kinds of proteins on the cell. One of the proteins is the IL-6 receptor which is a ligand binding protein to which IL-6 binds and has a molecular weight of about 80 kDa (Non-patent Documents 4 and 5). In addition to a membrane-bound form that penetrates and is expressed on the cell membrane, the IL-6 receptor is present as a soluble IL-6 receptor which mainly consists of the extracellular region of the membrane-bound form.

The other is the membrane protein gp130 which has a molecular weight of about 130 kDa and is involved in non-ligand binding signal transduction. The biological activity of IL-6 is transmitted into the cell through formation of the IL-6/IL-6 receptor complex by IL-6 and IL-6 receptor and binding of the complex with gp130 thereafter (Non-patent Document 6).

IL-6 inhibitors are substances that inhibit the transmission of IL-6 biological activity. Until now, antibodies against IL-6 (anti-IL-6 antibodies), antibodies against IL-6 receptors (anti-IL-6 receptor antibodies), antibodies against gp130 (anti-gp130 antibodies), IL-6 variants, partial peptides of IL-6 or IL-6 receptors, and such are known.

There are several reports regarding the anti-IL-6 receptor antibodies (Non-patent Documents 7 and 8, Patent Documents 1-3). A humanized PM-1 antibody, which had been obtained by transplanting into a human antibody, the complementarity determining region (CDR) of mouse antibody PM-1 (Non-patent Document 9), which is one of anti-IL-6 receptor antibodies, is known (Patent Document 4).

Information on prior-art documents related to the present invention is described below:

[Non-patent Document 1] Hirano, T. et al., Nature (1986) 324, 73-76
[Non-patent Document 2] Akira, S. et al., Adv. in Immunology (1993) 54, 1-78
[Non-patent Document 3] Lotz, M. et al., J. Exp. Med. (1988) 167, 1253-1258
[Non-patent Document 4] Taga, T. et al., J. Exp. Med. (1987) 166, 967-981
[Non-patent Document 5] Yamasaki, K. et al., Science (1988) 241, 825-828
[Non-patent Document 6] Taga, T. et al., Cell (1989) 58, 573-581
[Non-patent Document 7] Novick, D. et al., Hybridoma (1991) 10, 137-146
[Non-patent Document 8] Huang, Y. W. et al., Hybridoma (1993) 12, 621-630
[Non-patent Document 9] Hirata, Y. et al., J. Immunol. (1989) 143, 2900-2906
[Patent Document 1] International Patent Application Publication No. WO 95/09873

[Patent Document 2] French Patent Application No. FR 2694767
[Patent Document 3] U.S. Pat. No. 5,216,128
[Patent Document 4] WO 92/19759

DISCLOSURE OF THE INVENTION

[Problems to be Solved by the Invention]

In islet transplantation for treating diabetes it is important to improve islet viability by suppressing damage to transplanted islets at the time of transplantation. However, there are no effective methods to date. Further, there has been no previous assessment of whether anti-IL-6 receptor antibody, which is an IL-6 inhibitor, shows the effect of suppressing damage to transplanted islets after islet transplantation.

The present invention was achieved in view of the above background, and aims to provide agents for suppressing damage to transplanted islets, which comprise IL-6 inhibitors as active ingredients, and that are used in islet transplantation. Another objective of the present invention is to provide methods for suppressing damage to islets transplanted in to subjects, which comprise the step of administering IL-6 inhibitors to the subjects.

[Means for Solving the Problems]

To achieve the objectives described above, the present inventors tested whether anti-IL-6 receptor antibodies exerted the effect of suppressing damage to transplanted islets after islet transplantation.

First, the present inventors prepared diabetic mice as recipients by intravenously administering streptozotocin to male C57BL/6 mice.

Then, the diabetic recipient mice were transplanted with islets isolated from the pancreases of two mice (400 islets) or from a single mouse (200 islets). The results show that the transplantation of islets from the pancreases of two mice restored normal blood sugar levels and thus showed therapeutic effect for diabetes, while that from a single mouse did not restore normal blood sugar levels and the hyperglycemic state was maintained (FIGS. 2 and 3).

Meanwhile, when 500 µg of an anti-IL-6 receptor antibody (MR16-1) was intraperitoneally administered three times after transplantation of islets from a single mouse (200 islets), normal blood sugar levels were restored in all recipients after transplantation (FIG. 4). Alternatively, when an equal dose of an anti-IL-6 receptor antibody was administered once, normal blood sugar levels were restored in three-quarters of recipients (FIG. 5). When 200 µg of anti-IL-6 receptor antibody was administered once, normal blood sugar levels were restored in one-third of recipients (FIG. 6).

Administration of the anti-IL-6 receptor antibodies of the present invention was also found to suppress the production of inflammatory cytokines in infiltrating cells after transplantation.

The above findings show that anti-IL-6 receptor antibodies reduce damage to transplanted islets, improve islet viability, and correct hyperglycemia in recipients.

Specifically, the present inventors discovered for the first time that damage to transplanted islets after islet transplantation could be suppressed by using anti-IL-6 receptor antibodies according to the present invention, and they thus completed the present invention.

More specifically, the present invention provides the following [1] to [23]:

[1] An agent for suppressing damage to a transplanted islet after islet transplantation, which comprises an IL-6 inhibitor as an active ingredient;

[2] The agent for suppressing damage to a transplanted islet of [1], wherein the IL-6 inhibitor is an antibody that recognizes an IL-6;

[3] The agent for suppressing damage to a transplanted islet of [1], wherein the IL-6 inhibitor is an antibody that recognizes an IL-6 receptor;

[4] The agent for suppressing damage to a transplanted islet of [2] or [3], wherein the antibody is a monoclonal antibody;

[5] The agent for suppressing damage to a transplanted islet of any one of [2] to [4], wherein the antibody is an anti-human IL-6 antibody or an anti-human IL-6 receptor antibody;

[6] The agent for suppressing damage to a transplanted islet of any one of [2] to [5], wherein the antibody is a recombinant antibody;

[7] The agent for suppressing damage to a transplanted islet of [6], wherein the antibody is a chimeric, humanized, or human antibody;

[8] The agent for suppressing damage to a transplanted islet of any one of [1] to [7], which is used to treat diabetes;

[9] a method for suppressing damage to transplanted islets in an islet transplantation subject, which comprises the step of administering an IL-6 inhibitor to the subject;

[10] a method for improving viability of an islet in an islet transplantation subject, which comprises the step of administering an IL-6 inhibitor to the subject;

[11] the method of [9] or [10], wherein the IL-6 inhibitor is an antibody that recognizes an IL-6;

[12] the method of [9] or [10], wherein the IL-6 inhibitor is an antibody that recognizes an IL-6 receptor;

[13] the method of [11] or [12], wherein the antibody is a monoclonal antibody;

[14] the method of any one of [11] to [13], wherein the antibody is an anti-human IL-6 antibody or an anti-human IL-6 receptor antibody;

[15] the method of any one of [11] to [14], wherein the antibody is a recombinant antibody;

[16] the method of [15], wherein the antibody is a chimeric, humanized, or human antibody;

[17] use of an IL-6 inhibitor to produce agents for suppressing damage to a transplanted islet after islet transplantation;

[18] the use of [17], wherein the IL-6 inhibitor is an antibody that recognizes an IL-6;

[19] the use of [17], wherein the IL-6 inhibitor is an antibody that recognizes an IL-6 receptor;

[20] the use of [18] or [19], wherein the antibody is a monoclonal antibody;

[21] the use of any one of [18] to [20], wherein the antibody is an anti-human IL-6 antibody or an anti-human IL-6 receptor antibody;

[22] the use of any one of [18] to [21], wherein the antibody is a recombinant antibody; and

[23] the use of [22], wherein the antibody is a chimeric, humanized, or human antibody.

BEST MODE FOR CARRYING OUT THE INVENTION

Figure 1:
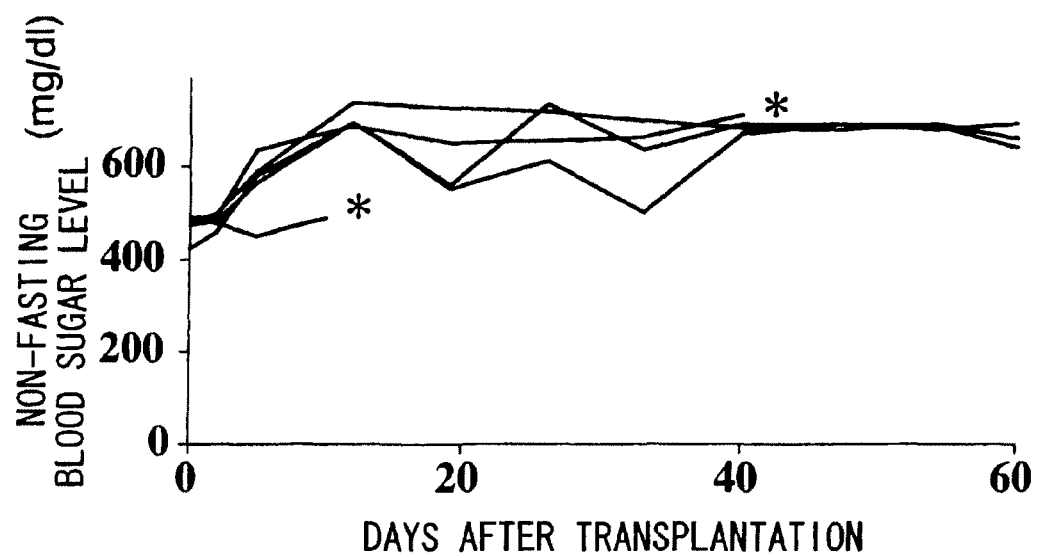
FIG. 1 is a graph showing changes in blood sugar levels in diabetic recipient mice that did not undergo islet transplantation.

The present inventors discovered that anti-IL-6 receptor antibody can suppress damage to transplanted islets after islet transplantation. The present invention is based on these findings.

The present invention relates to agents for suppressing damage to transplanted islets after islet transplantation, which comprise an IL-6 inhibitor as an active ingredient.

Herein, an "IL-6 inhibitor" is a substance that blocks IL-6-mediated signal transduction and inhibits IL-6 biological activity. Preferably, the IL-6 inhibitor is a substance that has inhibitory function against the binding of IL-6, IL-6 receptor, or gp130.

The IL-6 inhibitors of the present invention include, but are not limited to, for example, anti-IL-6 antibodies, anti-IL-6 receptor antibodies, anti-gp130 antibodies, IL-6 variants, soluble IL-6 receptor variants, and partial peptides of IL-6 or IL-6 receptors and low molecular weight compounds that show similar activities. Preferable IL-6 inhibitors of the present invention include antibodies that recognize IL-6 receptors.

The source of the antibody is not particularly restricted in the present invention; however, the antibody is preferably derived from mammals, and more preferably derived from human.

The anti-IL-6 antibody used in the present invention can be obtained as a polyclonal or monoclonal antibody via known means. In particular, monoclonal antibodies derived from mammals are preferred as the anti-IL-6 antibody used in the present invention. The monoclonal antibodies derived from mammals include those produced from hybridomas and those produced from hosts transformed with an expression vector that comprises an antibody gene by genetic engineering methods. By binding to IL-6, the antibody inhibits IL-6 from binding to an IL-6 receptor and blocks the transmission of IL-6 biological activity into the cell.

Such antibodies include, MH166 (Matsuda, T. et al., Eur. J. Immunol. (1988) 18, 951-956), SK2 antibody (Sato, K. et al., transaction of the 21$^{st}$ Annual Meeting of the Japanese Society for Immunology (1991) 21, 166), and so on.

Basically, anti-IL-6 antibody producing hybridomas can be prepared using known techniques as follows. Specifically, such hybridomas can be prepared by using IL-6 as a sensitizing antigen to carry out immunization by a conventional immunization method, fusing the obtained immune cells with known parent cells by a conventional cell fusion method, and screening for monoclonal antibody-producing cells by a conventional screening method.

More specifically, anti-IL-6 antibodies can be produced as follows. For example, human IL-6 used as the sensitizing antigen for obtaining antibody can be obtained using the IL-6 gene and/or amino acid sequences disclosed in Eur. J. Biochem. (1987) 168, 543-550; J. Immunol. (1988) 140, 1534-1541; and/or Agr. Biol. Chem. (1990) 54, 2685-2688.

After transforming an appropriate host cell with a known expression vector system inserted with an IL-6 gene sequence, the desired IL-6 protein is purified by a known method from the inside of the host cell or from the culture supernatant. This purified IL-6 protein may be used as the sensitizing antigen. Alternatively, a fusion protein of the IL-6 protein and another protein may be used as the sensitizing antigen.

Anti-IL6 receptor antibodies used for the present invention can be obtained as polyclonal or monoclonal antibodies by known methods. In particular, the anti-IL-6 receptor antibodies used in the present invention are preferably monoclonal antibodies derived from mammals. The monoclonal antibodies derived from mammals include those produced from hybridomas and those produced from hosts transformed with an expression vector that comprises an antibody gene by genetic engineering methods. By binding to an IL-6 receptor, the antibody inhibits IL-6 from binding to the IL-6 receptor and blocks the transmission of IL-6 biological activity into the cell.

Such antibodies include, MR16-1 antibody (Tamura, T. et al., Proc. Natl. Acad. Sci. USA (1993) 90, 11924-11928); PM-1 antibody (Hirata, Y. et al., J. Immunol. (1989) 143, 2900-2906); AUK12-20 antibody, AUK64-7 antibody and AUK146-15 antibody (WO 92/19759); and so on. Among them, the PM-1 antibody can be exemplified as a preferred monoclonal antibody against the human IL-6 receptor, and the MR16-1 antibody as a preferred monoclonal antibody against the mouse IL-6 receptor.

Basically, hybridomas producing an anti-IL-6 receptor monoclonal antibody can be prepared using known techniques as follows. Specifically, such hybridomas can be prepared by using an IL-6 receptor as the sensitizing antigen to carry out immunization by a conventional immunization method, fusing the obtained immune cells with a known parent cell by a conventional cell fusion method, and screening for monoclonal antibody-producing cells by a conventional screening method.

More specifically, anti-IL-6 receptor antibodies can be produced as follows. For example, a human IL-6 receptor or mouse IL-6 receptor used as the sensitizing antigen for obtaining antibody can be obtained using the IL-6 receptor genes and/or amino acid sequences disclosed in European Patent Application Publication No. EP 325474 and Japanese Patent Application Kokai Publication No. (JP-A) H03-155795 (unexamined, published Japanese patent application), respectively.

There exist two kinds of IL-6 receptor proteins, i.e., protein expressed on the cell membrane and protein separated from the cell membrane (soluble IL-6 receptor) (Yasukawa, K. et al., J. Biochem. (1990) 108, 673-676). The soluble IL-6 receptor consists essentially of the extracellular region of the cell membrane-bound IL-6 receptor, and differs from the membrane-bound IL-6 receptor in that it lacks the transmembrane region or both the transmembrane and intracellular regions. Any IL-6 receptor may be employed as the IL-6 receptor protein so long as it can be used as a sensitizing antigen for producing the anti-IL-6 receptor antibody utilized in the present invention.

After transforming an appropriate host cell with a known expression vector system inserted with an IL-6 receptor gene sequence, the desired IL-6 receptor protein is purified by a known method from the inside of the host cell or from the culture supernatant. This purified IL-6 receptor protein may be used as a sensitizing antigen. Alternatively, a cell expressing the IL-6 receptor or a fusion protein of the IL-6 receptor protein and another protein may be used as a sensitizing antigen.

Anti-gp130 antibodies used in the present invention can be obtained as polyclonal or monoclonal antibodies by known methods. In particular, the anti-gp130 antibodies used in the present invention are preferably monoclonal antibodies derived from mammals. The monoclonal antibodies derived from mammals include those produced from hybridomas and those produced from hosts transformed with an expression vector that comprises an antibody gene by genetic engineering methods. By binding to gp130, the antibody inhibits gp130 from binding to the IL-6/IL-6 receptor complex and blocks the transmission of IL-6 biological activity into the cell.

Such antibodies include, AM64 antibody (JP-A (Kokai) H03-219894); 4B11 antibody and 2H4 antibody (U.S. Pat. No. 5,571,513); B-S12 antibody and B-P8 antibody (JP-A (Kokai) H08-291199); and so on.

Basically, Anti-gp130 monoclonal antibody-producing hybridomas can be prepared using known techniques as follows. Specifically, such hybridomas can be prepared by using gp130 as a sensitizing antigen to carry out the immunization by a conventional immunization method, fusing the obtained immune cells with a known parent cell by a conventional cell fusion method, and screening for monoclonal antibody-producing cells by a conventional screening method.

More specifically, the monoclonal antibody can be produced as follows. For example, gp130 used as a sensitizing antigen for obtaining antibody can be obtained using the gp130 gene and/or amino acid sequence disclosed in European Patent Application Publication No. EP 411946.

After transforming an appropriate host cell with a known expression vector system inserted with a gp130 gene sequence, the desired gp130 protein is purified by a known method from the inside of the host cell or from the culture supernatant. This purified gp130 protein may be used as a sensitizing antigen. Alternatively, a cell expressing gp130 or a fusion protein of the gp130 protein and another protein may be used as a sensitizing antigen.

Mammals to be immunized with a sensitizing antigen are not particularly limited, but are preferably selected in consideration of the compatibility with the parent cell used for cell fusion. Generally, rodents such as mice, rats, and hamsters are used.

Immunization of animals with a sensitizing antigen is performed according to known methods. For example, as a general method, it is performed by injecting the sensitizing antigen intraperitoneally or subcutaneously into mammals. Specifically, the sensitizing antigen is preferably diluted or suspended in an appropriate amount of phosphate-buffered saline (PBS), physiological saline or such, mixed with an appropriate amount of a general adjuvant (e.g., Freund's complete adjuvant), emulsified, and then administered for several times every 4 to 21 days to a mammal. In addition, an appropriate carrier may be used for the immunization with a sensitizing antigen.

Following such immunization, an increased level of the desired antibody in serum is confirmed and then immune cells are obtained from the mammal for cell fusion. Preferred immune cells for cell fusion include, in particular, spleen cells.

For the mammalian myeloma cells to be used as a parent cell, i.e. a partner cell to be fused with the above immune cells, various known cell strains, for example, P3X63Ag8.653 (Kearney, J. F. et al., J. Immunol (1979) 123, 1548-1550), P3X63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), F0 (de St. Groth, S. F. et al., J. Immunol. Methods (1980) 35, 1-21), S194 (Trowbridge, I. S., J. Exp. Med. (1978) 148, 313-323), R210 (Galfre, G. et al., Nature (1979) 277, 131-133), and such are appropriately used.

Basically, cell fusion of the aforementioned immune cell and myeloma cell can be performed using known methods, for example, the method by Milstein et al. (Kohler, G. and Milstein, C., Methods Enzymol. (1981) 73, 3-46) and such.

More specifically, the aforementioned cell fusion is achieved in general nutrient culture medium under the presence of a cell fusion enhancing agent. For example, polyethylene glycol (PEG), Sendai virus (HVJ), and such are used as a fusion enhancing agent. Further, to enhance the fusion efficiency, auxiliary agents such as dimethyl sulfoxide may be added for use according to needs.

The ratio of immune cells and myeloma cells used is preferably, for example, 1 to 10 immune cells for each myeloma cell. The culture medium used for the aforementioned cell fusion is, for example, the RPMI1640 or MEM culture medium, which are suitable for the proliferation of the aforementioned myeloma cells. A general culture medium used for culturing this type of cell can also be used. Furthermore, serum supplements such as fetal calf serum (FCS) can be used in combination.

For cell fusion, the fusion cells (hybridomas) of interest are formed by mixing predetermined amounts of the aforementioned immune cell and myeloma cell well in the aforementioned culture medium, and then adding and mixing a concentration of 30 to 60% (w/v) PEG solution (e.g., a PEG solution with a mean molecular weight of about 1,000 to 6,000) pre-heated to about 37° C. Then, cell fusion agents and such that are unsuitable for the growth of hybridoma can be removed by repeating the steps of successively adding an appropriate culture medium and removing the supernatant by centrifugation.

The above hybridomas are selected by culturing cells in a general selection culture medium, for example, HAT culture medium (a culture medium containing hypoxanthine, aminopterin, and thymidine). Culturing in the HAT culture medium is continued for a sufficient period of time, generally for several days to several weeks, to kill cells other than the hybridomas of interest (unfused cells). Then, the standard limited dilution method is performed to screen and clone hybridomas that produce the antibody of interest.

In addition to the method of immunizing a non-human animal with an antigen for obtaining the aforementioned hybridomas, a desired human antibody that has the activity of binding to a desired antigen or antigen-expressing cell can be obtained by sensitizing a human lymphocyte with a desired antigen protein or antigen-expressing cell in vitro, and fusing the sensitized B lymphocyte with a human myeloma cell (e.g., U266) (see, Japanese Patent Application Kokoku Publication No. (JP-B) H01-59878 (examined, approved Japanese patent application published for opposition)). Furthermore, a desired human antibody can be obtained by administering the antigen or antigen-expressing cell to a transgenic animal that has a repertoire of human antibody genes and then following the aforementioned method (see, International Patent Application Publication Nos. WO 93/12227, WO 92/03918, WO 94/02602, WO 94/25585, WO 96/34096, and WO 96/33735).

The thus-prepared hybridomas which produce monoclonal antibodies can be subcultured in conventional culture medium and stored in liquid nitrogen for a long period.

For obtaining monoclonal antibodies from the aforementioned hybridomas, the following methods may be employed: (1) method where the hybridomas are cultured according to conventional methods and the antibodies are obtained as a culture supernatant; (2) method where the hybridomas are proliferated by administering them to a compatible mammal and the antibodies are obtained as ascites; and so on. The former method is preferred for obtaining antibodies with high purity, and the latter is preferred for large-scale production of antibodies.

For example, the preparation of anti-IL-6 receptor antibody-producing hybridomas can be performed by the method disclosed in JP-A (Kokai) H03-139293. The preparation can be performed by the method of injecting a PM-1 antibody-producing hybridoma into the abdominal cavity of a BALB/c mouse, obtaining ascite, and then purifying PM-1 antibody from the ascite, or the method of culturing the hybridoma in an appropriate medium (e.g., RPMI1640 medium containing 10% fetal bovine serum, and 5% BM-Condimed H1 (Boehringer Mannheim); hybridoma SFM medium (GIBCO-BRL); PFHM-II medium (GIBCO-BRL), etc.) and then obtaining PM-1 antibody from the culture supernatant.

A recombinant antibody can be used as a monoclonal antibody of the present invention, wherein the antibody is produced through genetic recombination techniques by cloning an antibody gene from a hybridoma, inserting the gene into an appropriate vector, and then introducing the vector into a host (see, for example, Borrebaeck, C. A. K. and Larrick, J. W., THERAPEUTIC MONOCLONAL ANTIBODIES, published in the United Kingdom by MACMILLAN PUBLISHERS LTD., 1990).

More specifically, mRNA coding for the variable (V) region of an antibody is isolated from a cell that produces the antibody of interest, such as a hybridoma. The isolation of mRNA can be performed by preparing total RNA according to known methods, such as the guanidine ultracentrifugation method (Chirgwin, J. M. et al., Biochemistry (1979) 18, 5294-5299) and the AGPC method (Chomczynski, P. et al., Anal. Biochem. (1987) 162, 156-159), and preparing mRNA using the mRNA Purification Kit (Pharmacia) and such. Alternatively, mRNA can be directly prepared using the QuickPrep mRNA Purification Kit (Pharmacia).

cDNA of the antibody V region is synthesized from the obtained mRNA using reverse transcriptase. The synthesis of cDNA may be achieved using the AMV Reverse Transcriptase First-strand cDNA Synthesis Kit and so on. Furthermore, to synthesize and amplify the cDNA, the 5'-RACE method (Frohman, M. A. et al., Proc. Natl. Acad. Sci. USA (1988) 85, 8998-9002; Belyavsky, A. et al., Nucleic Acids Res. (1989) 17, 2919-2932) using 5'-Ampli FINDER RACE Kit (Clontech) and PCR may be employed. The DNA fragment of interest is purified from the obtained PCR products and then ligated with a vector DNA. Then, a recombinant vector is prepared using the above DNA and introduced into *Escherichia coli* or such, and its colonies are selected to prepare the desired recombinant vector. The nucleotide sequence of the DNA of interest is confirmed by, for example, the dideoxy method.

When a DNA encoding the V region of an antibody of interest is obtained, the DNA is ligated with a DNA that encodes a desired antibody constant region (C region), and inserted into an expression vector. Alternatively, the DNA encoding the antibody V region may be inserted into an expression vector comprising the DNA of an antibody C region.

To produce an antibody to be used in the present invention, as described below, the antibody gene is inserted into an expression vector so that it is expressed under the control of the expression regulating region, for example, enhancer and promoter. Then, the antibody can be expressed by transforming a host cell with this expression vector.

In the present invention, to decrease heteroantigenicity against human and such, artificially modified genetic recombinant antibodies, for example, chimeric antibodies, humanized antibodies, or human antibodies, can be used. These modified antibodies can be prepared using known methods.

A chimeric antibody can be obtained by ligating the antibody V region-encoding DNA obtained as above with a human antibody C region-encoding DNA, inserting the DNA into an expression vector and introducing it into a host for production (see, European Patent Application Publication No. EP 125023; International Patent Application Publication No. WO 92/19759). This known method can be used to obtain chimeric antibodies useful for the present invention.

Humanized antibodies are also referred to as reshaped human antibodies, and are antibodies wherein the complementarity determining regions (CDRs) of an antibody from a mammal other than human (e.g., mouse antibody) are transferred into the CDRs of a human antibody. General methods for this gene recombination are also known (see, European Patent Application Publication No. EP 125023, International Patent Application Publication No. WO 92/19759).

More specifically, a DNA sequence designed such that the CDRs of a mouse antibody are ligated with the framework regions (FRs) of a human antibody is synthesized by PCR from several oligonucleotides that had been produced to contain overlapping portions at their termini. The obtained DNA is ligated with a human antibody C region-encoding DNA and then inserted into an expression vector. The expression vector is introduced into a host to produce the humanized antibody (see, European Patent Application Publication No. EP 239400, International Patent Application Publication No. WO 92/19759).

The human antibody FRs to be ligated via the CDRs are selected so that the CDRs form a suitable antigen binding site. The amino acid(s) within the FRs of the antibody variable regions may be substituted as necessary so that the CDRs of the reshaped human antibody form an appropriate antigen binding site (Sato, K. et al., Cancer Res. (1993) 53, 851-856).

Human antibody C regions are used for the chimeric and humanized antibodies, and include Cγ. For example, Cγ1, Cγ2, Cγ3, or Cγ4 may be used. Furthermore, to improve the stability of the antibody or its production, the human antibody C regions may be modified.

Chimeric antibodies consist of the variable region of an antibody derived from non-human mammals and a human antibody-derived C region; and humanized antibodies consist of the CDRs of an antibody derived from non-human mammals and the framework regions and C regions derived from a human antibody. Both have reduced antigenicity in human body, and are therefore are useful as antibodies to be used in the present invention.

Preferred specific examples of humanized antibodies used in the present invention include a humanized PM-1 antibody (see, International Patent Application Publication No. WO 92/19759).

Furthermore, in addition to the aforementioned method for obtaining a human antibody, techniques for obtaining human antibodies by panning using a human antibody library are also known. For example, it is possible to express the variable regions of human antibodies on the surface of phages as single chain antibodies (scFv) by the phage display method, and then select antigen-binding phages. By analyzing genes of the selected phages, DNA sequences coding for the human antibody variable regions that bind to the antigen can be determined. Once the DNA sequence of an scFv that binds to the antigen is revealed, an appropriate expression vector comprising the sequence can be constructed to obtain an human antibody. These methods are already known, and the publications of WO 92/01047, WO 92/20791, W093/06213, WO 93/11236, WO 93/19172, WO 95/01438, and WO 95/15388 can be used as reference.

The above-constructed antibody gene can be expressed according to conventional methods. When a mammalian cell is used, the antibody gene can be expressed using a DNA in which the antibody gene to be expressed is functionally ligated to a useful commonly used promoter and a poly A signal downstream of the antibody gene, or a vector comprising the DNA. Examples of a promoter/enhancer include the human cytomegalovirus immediate early promoter/enhancer.

Furthermore, other promoters/enhancers that can be utilized for expressing the antibody to be used in the present invention include viral promoters/enhancers from retrovirus, polyoma virus, adenovirus, simian virus 40 (SV40), and such; and mammalian cell-derived promoters/enhancers such as human elongation factor 1α (HEF1α).

For example, when the SV40 promoter/enhancer is used, the expression can be easily performed by following the method by Mulligan et al. (Mulligan, R. C. et al., Nature (1979) 277, 108-114). Alternatively, in the case of the HEF1α promoter/enhancer, the method by Mizushima et al. (Mizushima, S. and Nagata S., Nucleic Acids Res. (1990) 18, 5322) can be used.

When E. coli is used, the antibody gene can be expressed by functionally ligating a conventional useful promoter, a signal sequence for antibody secretion, and the antibody gene to be expressed. Examples of a promoter include the lacZ promoter, araB promoter and such. When the lacZ promoter is used, the expression can be performed according to the method by Ward et al. (Ward, E. S. et al., Nature (1989) 341, 544-546; Ward, E. S. et al., FASEB J. (1992) 6, 2422-2427); and the araB promoter may be used according to the method by Better et al. (Better, M. et al., Science (1988) 240, 1041-1043).

When the antibody is produced into the periplasm of E. coli, the pel B signal sequence (Lei, S. P. et al., J. Bacteriol. (1987) 169, 4379-4383) may be used as the signal sequence for antibody secretion. The antibody produced into the periplasm is isolated, and then used after appropriately refolding the antibody structure (see, e.g., WO 96/30394).

As the replication origin, those derived from SV40, polyoma virus, adenovirus, bovine papilloma virus (BPV) and such may be used. In addition, for enhancing the gene copy number in a host cell system, the expression vector may comprise the aminoglycoside phosphotransferase (APH) gene, thymidine kinase (TK) gene, E. coli xanthine-guanine phosphoribosyltransferase (Ecogpt) gene, dihydrofolate reductase (dhfr) gene, or such as a selection marker.

Any production system may be used for preparing the antibodies to be used in the present invention. The production systems for antibody preparation include in vitro and in vivo production systems. In vitro production systems include those utilizing eukaryotic cells or prokaryotic cells.

Production systems using eukaryotic cells include those utilizing animal cells, plant cells, or fungal cells. Such animal cells include (1) Mammalian cells, for example, CHO, COS, myeloma, baby hamster kidney (BHK), HeLa, Vero, and such; (2) amphibian cells, for example, *Xenopus* oocyte; and (3) insect cells, for example, sf9, sf21, Tn5, and such. Known plant cells include cells derived from *Nicotiana tabacum*, which may be cultured as callus. Known fungal cells include yeast such as *Saccharomyces* (e.g., *S. cerevisiae*), mold fungi such as *Aspergillus* (e.g., *A. niger*), and such.

Production systems using prokaryotic cells include those utilizing bacterial cells. Known bacterial cells include *E. coli* and *Bacillus subtilis*.

Antibodies can be obtained by introducing an antibody gene of interest into these cells by transformation, and culturing the transformed cells in vitro. The culturing is conducted according to known methods. For example, DMEM, MEM, RPMI1640, IMDM may be used as the culture medium, and serum supplements, such as FCS, may be used in combination. Furthermore, a cell introduced with an antibody gene may be transferred into the abdominal cavity or such of an animal to produce an antibody in vivo.

On the other hand, in vivo production systems include those utilizing animals or plants. Production systems using animals include those that utilize mammals or insects.

Mammals that can be used include goats, pigs, sheep, mice, bovines and such (Vicki Glaser, SPECTRUM Biotechnology Applications, 1993). Further, insects that can be used include silkworms. When using plants, for example, tobacco may be used.

An antibody gene is introduced into these animals or plants, and an antibody is produced in the body of the animals or plants and then recovered. For example, the antibody gene is prepared as a fusion gene by inserting the gene in the middle of a gene encoding a protein, such as goat β casein, which is uniquely produced into milk. A DNA fragment comprising the antibody gene-inserted fusion gene is injected into a goat embryo, and the embryo is introduced into a female goat. The desired antibody is obtained from the milk produced from the transgenic animal born from the goat that received the embryo, or produced from progenies of the animal. To increase the amount of milk that contains the desired antibody produced from the transgenic goat, hormones may by appropriately used on the transgenic goat (Ebert, K. M. et al., Bio/Technology (1994) 12, 699-702).

Furthermore, when a silkworm is used, it is infected with baculovirus inserted with the desired antibody gene, and the desired antibody is obtained from the body fluid of this silkworm (Maeda, S. et al., Nature (1985) 315, 592-594). Moreover, when tobacco is used, the desired antibody gene is inserted into a plant expression vector (e.g., pMON530) and the vector is introduced into bacteria such as *Agrobacterium*

*tumefaciens*. This bacterium is used to infect tobacco (e.g., *Nicotiana tabacum*) to obtain the desired antibody from the leaves of this tobacco (Julian, K.-C. Ma et al., Eur. J. Immunol. (1994) 24, 131-138).

When producing an antibody in in vitro or in vivo production systems as described above, DNAs encoding the antibody heavy chain (H chain) and light chain (L chain) may be inserted into separate expression vectors and a host is then co-transformed with the vectors. Alternatively, the DNAs may be inserted into a single expression vector for transforming a host (see, International Patent Application Publication No. WO 94/11523).

The antibodies used in the present invention may be antibody fragments or modified products thereof so long as they can be suitably used in the present invention. For example, antibody fragments include Fab, F(ab')2, Fv, and single chain Fv (scFv) in which the Fvs of the H and L chains are linked via an appropriate linker.

Specifically, the antibody fragments are produced by treating an antibody with an enzyme, for example, papain or pepsin, or alternatively, genes encoding these fragments are constructed, introduced into expression vectors, and expressed in an appropriate host cell (see, e.g., Co, M. S. et al., J. Immunol. (1994) 152, 2968-2976; Better, M. & Horwitz, A. H., Methods in Enzymology (1989) 178, 476-496; Plueckthun, A. & Skerra, A., Methods in Enzymology (1989) 178, 497-515; Lamoyi, E., Methods in Enzymology (1989) 121, 652-663; Rousseaux, J. et al., Methods in Enzymology (1989) 121, 663-666; Bird, R. E. et al., TIBTECH (1991) 9, 132-137).

An scFv can be obtained by linking the H-chain V region and the L-chain V region of an antibody. In the scFv, the H-chain V region and the L-chain V region are linked via a linker, preferably via a peptide linker (Huston, J. S. et al., Proc. Natl. Acad. Sci. USA (1988) 85, 5879-5883). The V regions of the H and L chains in an scFv may be derived from any of the antibodies described above. Peptide linkers for linking the V regions include, for example, an arbitrary single chain peptide consisting of 12 to 19 amino acid residues.

An scFv-encoding DNA can be obtained by using the DNA encoding the H chain or its V region and the DNA encoding the L chain or its V region of the aforementioned antibodies as templates, PCR amplifying the DNA portion that encodes the desired amino acid sequence in the template sequence using primers that define the termini of the portion, and then further amplifying the amplified DNA portion with a peptide linker portion-encoding DNA and primer pairs that link both ends of the linker to the H chain and L chain.

Furthermore, once an scFv-encoding DNA has been obtained, an expression vector comprising the DNA and a host transformed with the vector can be obtained according to conventional methods. In addition, the scFv can be obtained according to conventional methods using the host.

Similarly as above, these antibody fragments can be produced from the host by obtaining and expressing their genes. Herein, "antibody" encompasses these antibody fragments.

As a modified antibody, an antibody bound to various molecules, such as polyethylene glycol (PEG), may also be used. Herein, "antibody" encompasses these modified antibodies. These modified antibodies can be obtained by chemically modifying the obtained antibodies. Such methods are already established in the art.

The antibodies produced and expressed as above can be isolated from the inside or outside of the cell or from host, and purified to homogeneity. The isolation and/or purification of the antibodies used for the present invention can be performed by affinity chromatography. Columns to be used for the affinity chromatography include, for example, protein A column and protein G column. Carriers used for the protein A column include, for example, HyperD, POROS, Sepharose F.F. and such. In addition to the above, other methods used for the isolation and/or purification of common proteins may be used, and are not limited in any way.

For example, the antibodies used for the present invention may be isolated and/or purified by appropriately selecting and combining chromatographies besides affinity chromatography, filters, ultrafiltration, salting-out, dialysis, and such. Chromatographies include, for example, ion-exchange chromatography, hydrophobic chromatography, gel filtration, and such. These chromatographies can be applied to high performance liquid chromatography (HPLC). Alternatively, reverse phase HPLC may be used.

Concentration of the antibodies as obtained above can be determined by absorbance measurement, ELISA, or such. Specifically, the absorbance is determined by appropriately diluting the antibody solution with PBS(−), measuring the absorbance at 280 nm, and calculating the concentration (1.35 OD=1 mg/ml). Alternatively, when using ELISA, the measurement can be performed as follows. Specifically, 100 µl of goat anti-human IgG (TAG) diluted to 1 µg/ml with 0.1 M bicarbonate buffer (pH 9.6) is added to a 96-well plate (Nunc) and incubated overnight at 4° C. to immobilize the antibody. After blocking, 100 µl of an appropriately diluted antibody of the present invention or an appropriately diluted sample comprising the antibody, and human IgG (CAPPEL) are added as a standard, and incubated for one hour at room temperature.

After washing, 100 µl of 5,000× diluted alkaline phosphatase-labeled anti-human IgG (BIO SOURCE) is added and incubated for one hour at room temperature. After another wash, substrate solution is added and incubated, and the absorbance at 405 nm is measured using MICROPLATE READER Model 3550 (Bio-Rad) to calculate the concentration of the antibody of interest.

IL-6 variants used in the present invention are substances that have the activity to bind to an IL-6 receptor and which do not transmit IL-6 biological activity. That is, the IL-6 variants compete with IL-6 to bind to IL-6 receptors, but fail to transmit IL-6 biological activity, hence blocking IL-6-mediated signal transduction.

The IL-6 variants are produced by introducing mutation(s) through substitution of amino acid residues in the amino acid sequence of IL-6. The origin of IL-6 used as the base of the IL-6 variants is not limited; however, it is preferably human IL-6 when considering its antigenicity and such.

More specifically, amino acid substitution is performed by predicting the secondary structure of the IL-6 amino acid sequence using known molecular modeling programs (e.g., WHATIF; Vriend et al., J. Mol. Graphics (1990) 8, 52-56), and further assessing the influence of the substituted amino acid residue(s) on the whole molecule. After determining the appropriate amino acid residue to be substituted, commonly performed PCR methods are carried out using the human IL-6 gene-encoding nucleotide sequence as a template to introduce mutations so that amino acids are substituted, and thereby an IL-6 variant-encoding gene is obtained. If needed, this gene is inserted into an appropriate expression vector, and the IL-6 variant can be obtained by applying the aforementioned methods for expression, production, and purification of recombinant antibodies.

Specific examples of the IL-6 variants are disclosed in Brakenhoff et al., J. Biol. Chem. (1994) 269, 86-93, Savino et al., EMBO J. (1994) 13, 1357-1367, WO 96/18648, and WO 96/17869.

Partial peptides of IL-6 and partial peptides of IL-6 receptors to be used in the present invention are substances that have the activity to bind to IL-6 receptors and IL-6, respectively, and which do not transmit IL-6 biological activity. Namely, by binding to and capturing an IL-6 receptor or IL-6, the IL-6 partial peptide or the IL-6 receptor partial peptide specifically inhibits IL-6 from binding to the IL-6 receptor. As a result, the biological activity of IL-6 is not transmitted, and therefore IL-6-mediated signal transduction is blocked.

The partial peptides of IL-6 or IL-6 receptor are peptides that comprise part or all of the amino acid sequence of the region of the IL-6 or IL-6 receptor amino acid sequence that is involved in the binding of IL-6 and IL-6 receptor. Such peptides usually comprise 10 to 80, preferably 20 to 50, more preferably 20 to 40 amino acid residues.

The IL-6 partial peptides or IL-6 receptor partial peptides can be produced according to generally known methods, for example, genetic engineering techniques or peptide synthesis method, by specifying the region of the IL-6 or IL-6 receptor amino acid sequence that is involved in the binding of IL-6 and IL-6 receptor, and using a portion or whole of the amino acid sequence of the specified region.

When preparing an IL-6 partial peptide or IL-6 receptor partial peptide by a genetic engineering method, a DNA sequence encoding the desired peptide is inserted into an expression vector, and then the peptide can be obtained by applying the aforementioned methods for expressing, producing, and purifying recombinant antibodies.

To produce an IL-6 partial peptide or IL-6 receptor partial peptide by peptide synthesis methods, the generally used peptide synthesis methods, for example, solid phase synthesis methods or liquid phase synthesis methods may be used.

Specifically, the synthesis can be performed following the method described in "Continuation of Development of Pharmaceuticals, Vol. 14, Peptide Synthesis (in Japanese) (ed. Haruaki Yajima, 1991, Hirokawa Shoten)". As a solid phase synthesis method, for example, the following method can be employed: the amino acid corresponding to the C terminus of the peptide to be synthesized is bound to a support that is insoluble in organic solvents, then elongating the peptide strand by alternately repeating (1) the reaction of condensing amino acids whose α-amino groups and branch chain functional groups are protected with appropriate protecting groups one at a time in a C to N-terminal direction; and (2) the reaction of removing protecting groups from the α-amino groups of the resin-bound amino acid or peptide. The solid phase peptide synthesis is broadly classified into the Boc method and the Fmoc method based on the type of protecting group used.

After the protein of interest is synthesized as above, deprotection reaction and reaction to cleave the peptide strand from the support are carried out. For the cleavage reaction of the peptide strand, in general, hydrogen fluoride or trifluoromethane sulfonic acid is used for the Boc method, and TFA for the Fmoc method. According to the Boc method, for example, the above-mentioned protected peptide resin is treated in hydrogen fluoride under the presence of anisole. Then, the peptide is recovered by removing the protecting group and cleaving the peptide from the support. By freeze-drying the recovered peptide, a crude peptide can be obtained. On the other hand, in the Fmoc method, for example, the deprotection reaction and the reaction to cleave the peptide strand from the support can be performed in TFA by a similar method as described above.

The obtained crude peptide can be separated and/or purified by applying HPLC. Elution may be performed under optimum conditions using a water-acetonitrile solvent system, which is generally used for protein purification. The fractions corresponding to the peaks of the obtained chromatographic profile are collected and freeze-dried. Thus, purified peptide fractions are identified by molecular weight analysis via mass spectrum analysis, amino acid composition analysis, amino acid sequence analysis, or such.

Specific examples of IL-6 partial peptides and IL-6 receptor partial peptides are disclosed in JP-A (Kokai) H02-188600, JP-A (Kokai) H07-324097, JP-A (Kokai) H08-311098, and United States Patent Publication No. U.S. Pat. No. 5,210,075.

The antibodies used in the present invention may also be conjugated antibodies which are bound to various molecules, such as polyethylene glycol (PEG), radioactive substances, and toxins. Such conjugated antibodies can be obtained by chemically modifying the obtained antibodies. Methods for modifying antibodies are already established in the art. The "antibodies" of the present invention encompass these conjugated antibodies.

The agents of the present invention for suppressing damage to transplanted islets after islet transplantation can be used to treat diabetes. Diabetes includes type 1 diabetes, type 2 diabetes, pancreatic diabetes, gestational diabetes and such. The above-described diabetes also includes secondary diabetes caused by pancreatitis or induced by the use of steroidal drugs, and diabetes due to specific causes, such as diabetes caused by abnormalities in particular genes.

The agents of the present invention for suppressing damage to transplanted islets can be used in islet transplantation. Islet transplantation includes islet transplantation from brain-dead donors, from donors under cardiac arrest, and from living donors.

Islet transplantation according to the present invention may be both isografts and allografts. Isografts are transplantations between animals of a homogenous system, which in humans is transplantation between identical twins. Allografts are transplantations between individuals of the same species that are genetically different, which in humans is transplantation between completely unrelated individuals or between diovular twins. In the present invention, the activity of IL-6 inhibitors in inhibiting the transduction of IL-6 signal can be evaluated by conventional methods. Specifically, IL-6 is added to cultures of IL-6-dependent human myeloma cell lines (S6B45 and KPMM2), human Lennert T lymphoma cell line KT3, or IL-6-dependent cell line MH60.BSF2; and the $^3$H-thymidine uptake by the IL-6-dependent cells is measured in the presence of an IL-6 inhibitor. Alternatively, IL-6 receptor-expressing U266 cells are cultured, and $^{125}$I-labeled IL-6 and an IL-6 inhibitor are added to the culture at the same time; and then $^{125}$I-labeled IL-6 bound to the IL-6 receptor-expressing cells is quantified. In addition to the IL-6 inhibitor group, a negative control group that does not contain the IL-6 inhibitor is included in the assay system described above. The activity of the IL-6 inhibitor to inhibit IL-6 can be evaluated by comparing the results of both groups.

As shown below in the Examples, administration of an anti-IL-6 receptor antibody was found to suppress damage to transplanted islets after islet transplantation. This finding suggests that IL-6 inhibitors such as anti-IL-6 receptor antibodies are useful as agents for suppressing damage to transplanted islets after islet transplantation.

Subjects to be administered with the agents of the present invention for suppressing damage to transplanted islets are mammals. The mammals are preferably humans.

The agents of the present invention for suppressing damage to transplanted islets can be administered as pharmaceuticals, and may be administered systemically or locally via oral or parenteral administration. For example, intravenous injection such as drip infusion, intramuscular injection, intraperitoneal injection, subcutaneous injection, suppository, enema, oral enteric tablets, or the like can be selected. An appropriate administration method can be selected depending on the patient's age and symptoms. The effective dose per administration is selected from the range of 0.01 to 100 mg/kg body weight. Alternatively, the dose may be selected from the range of 1 to 1000 mg/patient, preferably from the range of 5 to 50 mg/patient. A preferred dose and administration method are as follows: for example, when an anti-IL-6 receptor antibody is used, the effective dose is an amount such that free antibody is present in the blood. Specifically, a dose of 0.5 to 40 mg/kg body weight/month (four weeks), preferably 1 to 20 mg/kg body weight/month is administered via intravenous injection such as drip infusion, subcutaneous injection or such, once to several times a month, for example, twice a week, once a week, once every two weeks, or once every four weeks. The administration schedule may be adjusted by, for example, extending the administration interval of twice a week or once a week to once every two weeks, once every three weeks, or once every four weeks, while monitoring the condition after transplantation and changes in the blood test values.

In the present invention, the agents for suppressing damage to transplanted islets may contain pharmaceutically acceptable carriers, such as preservatives and stabilizers. The "pharmaceutically acceptable carriers" refer to materials that can be co-administered with an above-described agent; and may or may not itself produce the above-described effect of suppressing damage to transplanted islets. Alternatively, the carriers may be materials that do not have the effect of suppressing damage to transplanted islets, but produce an additive or synergistic stabilizing effect when used in combination with an IL-6 inhibitor.

Such pharmaceutically acceptable materials include, for example, sterile water, physiological saline, stabilizers, excipients, buffers, preservatives, detergents, chelating agents (EDTA and such), and binders.

In the present invention, detergents include non-ionic detergents, and typical examples of such include sorbitan fatty acid esters such as sorbitan monocaprylate, sorbitan monolaurate, and sorbitan monopalmitate; glycerin fatty acid esters such as glycerin monocaprylate, glycerin monomyristate and glycerin monostearate; polyglycerin fatty acid esters such as decaglyceryl monostearate, decaglyceryl distearate, and decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, and polyoxyethylene sorbitan tristearate; polyoxyethylene sorbit fatty acid esters such as polyoxyethylene sorbit tetrastearate and polyoxyethylene sorbit tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol, polyoxyethylene polyoxypropylene propyl ether, and polyoxyethylene polyoxypropylene cetyl ether; polyoxyethylene alkyl phenyl ethers such as polyoxyethylene nonylphenyl ether; polyoxyethylene hardened castor oils such as polyoxyethylene castor oil and polyoxyethylene hardened castor oil (polyoxyethylene hydrogenated castor oil); polyoxyethylene beeswax derivatives such as polyoxyethylene sorbit beeswax; polyoxyethylene lanolin derivatives such as polyoxyethylene lanolin; and polyoxyethylene fatty acid amides and such with an HLB of 6 to 18, such as polyoxyethylene stearic acid amide.

Detergents also include anionic detergents, and typical examples of such include, for example, alkylsulfates having an alkyl group with 10 to 18 carbon atoms, such as sodium cetylsulfate, sodium laurylsulfate, and sodium oleylsulfate; polyoxyethylene alkyl ether sulfates in which the alkyl group has 10 to 18 carbon atoms and the average molar number of added ethylene oxide is 2 to 4, such as sodium polyoxyethylene lauryl sulfate; alkyl sulfosuccinate ester salts having an alkyl group with 8 to 18 carbon atoms, such as sodium lauryl sulfosuccinate ester; natural detergents, for example, lecithin; glycerophospholipids; sphingo-phospholipids such as sphingomyelin; and sucrose fatty acid esters in which the fatty acids have 12 to 18 carbon atoms.

One, two or more of the detergents described above can be combined and added to the agents of the present invention. Detergents that are preferably used in the preparations of the present invention include polyoxyethylene sorbitan fatty acid esters, such as polysorbates 20, 40, 60, and 80. Polysorbates 20 and 80 are particularly preferred. Polyoxyethylene polyoxypropylene glycols, such as poloxamer (Pluronic F-68® and such), are also preferred.

The amount of detergent added varies depending on the type of detergent used. When polysorbate 20 or 80 is used, the amount is in general in the range of 0.001 to 100 mg/ml, preferably in the range of 0.003 to 50 mg/ml, more preferably in the range of 0.005 to 2 mg/ml.

In the present invention, buffers includes phosphate, citrate buffer, acetic acid, malic acid, tartaric acid, succinic acid, lactic acid, potassium phosphate, gluconic acid, capric acid, deoxycholic acid, salicylic acid, triethanolamine, fumaric acid, and other organic acids; and carbonic acid buffer, Tris buffer, histidine buffer, and imidazole buffer.

Liquid preparations may be formulated by dissolving the agents in aqueous buffers known in the field of liquid preparations. The buffer concentration is in general in the range of 1 to 500 mM, preferably in the range of 5 to 100 mM, more preferably in the range of 10 to 20 mM.

The agents of the present invention may also comprise other low-molecular-weight polypeptides; proteins such as serum albumin, gelatin, and immunoglobulin; amino acids; sugars and carbohydrates such as polysaccharides and monosaccharides, sugar alcohols, and such.

Herein, amino acids include basic amino acids, for example, arginine, lysine, histidine, and ornithine, and inorganic salts of these amino acids (preferably hydrochloride salts, and phosphate salts, namely phosphate amino acids). When free amino acids are used, the pH is adjusted to a preferred value by adding appropriate physiologically acceptable buffering substances, for example, inorganic acids, in particular hydrochloric acid, phosphoric acid, sulfuric acid, acetic acid, and formic acid, and salts thereof. In this case, the use of phosphate is particularly beneficial because it gives quite stable freeze-dried products. Phosphate is particularly advantageous when preparations do not substantially contain organic acids, such as malic acid, tartaric acid, citric acid, succinic acid, and fumaric acid, or do not contain corresponding anions (malate ion, tartrate ion, citrate ion, succinate ion, fumarate ion, and such). Preferred amino acids are arginine, lysine, histidine, and ornithine. Furthermore, it is possible to use acidic amino acids, for example, glutamic acid and aspartic acid, and salts thereof (preferably sodium salts); neutral amino acids, for example, isoleucine, leucine, glycine, serine, threonine, valine, methionine, cysteine, and alanine; and aromatic amino acids, for example, phenylalanine, tyrosine, tryptophan, and its derivative, N-acetyl tryptophan.

Herein, sugars and carbohydrates such as polysaccharides and monosaccharides include, for example, dextran, glucose, fructose, lactose, xylose, mannose, maltose, sucrose, trehalose, and raffinose.

Herein, sugar alcohols include, for example, mannitol, sorbitol, and inositol.

When the agents of the present invention are prepared as aqueous solutions for injection, the agents may be mixed with, for example, physiological saline, and/or isotonic solution containing glucose or other auxiliary agents (such as D-sorbitol, D-mannose, D-mannitol, and sodium chloride). The aqueous solutions may be used in combination with appropriate solubilizing agents such as alcohols (ethanol and such), polyalcohols (propylene glycol, PEG, and such), or non-ionic detergents (polysorbate 80 and HCO-50).

The agents may further comprise, if required, diluents, solubilizers, pH adjusters, soothing agents, sulfur-containing reducing agents, antioxidants, and such.

Herein, the sulfur-containing reducing agents include, for example, compounds comprising sulfhydryl groups, such as N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and thioalkanoic acids having 1 to 7 carbon atoms.

Moreover, the antioxidants in the present invention include, for example, erythorbic acid, dibutylhydroxy toluene, butylhydroxy anisole, α-tocopherol, tocopherol acetate, L-ascorbic acid and salts thereof, L-ascorbic acid palmitate, L-ascorbic acid stearate, sodium hydrogen sulfite, sodium sulfite, triamyl gallate, propyl gallate, and chelating agents such as disodium ethylenediamine tetraacetate (EDTA), sodium pyrophosphate, and sodium metaphosphate.

If required, the agents may be encapsulated in microcapsules (microcapsules of hydroxymethylcellulose, gelatin, poly[methylmethacrylic acid] or such) or prepared as colloidal drug delivery systems (liposome, albumin microspheres, microemulsion, nano-particles, nano-capsules, and such) (see "Remington's Pharmaceutical Science $16^{th}$ edition", Oslo Ed., 1980, and the like). Furthermore, methods for preparing agents as sustained-release agents are also known, and are applicable to the present invention (Langer et al., J. Biomed. Mater. Res. 1981, 15: 167-277; Langer, Chem. Tech. 1982, 12: 98-105; U.S. Pat. No. 3,773,919; European Patent Application No. (EP) 58,481; Sidman et al., Biopolymers 1983, 22: 547-556; and EP 133,988).

Pharmaceutically acceptable carriers used are appropriately selected from those described above or combined depending on the type of dosage form, but are not limited thereto.

The present invention relates to methods for suppressing damage to transplanted islets, which comprise the step of administering an IL-6 inhibitor to subjects of islet transplantation. Further, the present invention relates to methods for improving the survival of transplanted islets in the subject, which comprise the step of administering an IL-6 inhibitor to subjects of islet transplantation.

Herein, the "subject" refers to organisms, body parts of the organisms, or an excised or delivered part of the organisms to be administered with an agent of the present invention for suppressing damage to transplanted islets. The organisms include animals (for example, human, domestic animal species, and wild animals) but are not particularly limited.

The "body parts of the organisms" are not particularly limited, but preferably include organs to be transplanted with the islets, greater omentum, subrenal capsule, and mesenterium. In the present invention, organs to be transplanted with the islets include liver, and more specifically, the liver blood vessels.

Herein, "administration" includes oral and parenteral administrations. Oral administration includes, for example, administration of oral agents. Such oral agents include, for example, granule, powder, tablet, capsule, solution, emulsion, and suspension.

Parenteral administration includes, for example, administration of injections. Such injections include, for example, subcutaneous injection, intramuscular injection, and intraperitoneal injection. Meanwhile, the effects of the methods of the present invention can be achieved by introducing genes comprising oligonucleotides to be administered to living bodies using gene therapy techniques. Alternatively, the agents of the present invention may be administered locally to intended areas of treatment. For example, the agents can be administered by local injection during surgery, use of catheters, or targeted gene delivery of DNA encoding a peptide of the present invention.

The suppressing agents of the present invention may be administered to subjects prior to organ transplantation, at the time of organ transplantation, or after organ transplantation. Further, the suppressing agents may be administered once or repeatedly.

Alternatively, when administered to an excised or delivered part of an organism, the suppressing agents of the present invention may be "contacted" with the organism part.

In the present invention, "contacting" is performed according to the condition of the organism. Examples include spraying the suppressing agents of the present invention over the organism parts, and adding the suppressing agents of the present invention to crushed organism parts, but are not limited thereto. When the organism part is cultured cells, the above-mentioned "contact" can be achieved by adding the suppressing agents of the present invention to culture medium of these cells, or by introducing DNAs comprising oligonucleotides of the present invention into cells that constitute the organism part.

When conducting the methods of the present invention, the suppressing agents of the present invention may be administered as parts of pharmaceutical compositions in combination with at least one known chemotherapeutant. Alternatively, the suppressing agents of the present invention may be administered simultaneously with at least one known immunosuppressant. In one embodiment, the known chemotherapeutants and the suppressing agents of the present invention may be administered virtually simultaneously.

The suppressing agents of the present invention may be administered to sites of islet transplantation after the islets have been transplanted, or may be administered to targets at the same time as the islets. Alternatively, the agents may be added to islets in vitro, prior to transplantation.

Herein, the phrase "suppression of damage to transplanted islets" means that damage to transplanted islets is suppressed and viability is improved. The phrase "suppression of damage to transplanted islets" also comprises suppression of natural immune responses accompanying transplantation.

Suppression of damage to transplanted islets can be confirmed by measuring blood sugar levels in living bodies, according to the methods described in the Examples. Blood sugar levels can be measured, for example, by collecting blood from the orbital sinus, and determining blood sugar levels using Beckman Glucose Analyzer after plasma skimming.

When administration of the agents of the present invention for suppressing damage to transplanted islets causes a sustained decrease in blood sugar level, damage to transplanted islets is regarded as suppressed. Alternatively, when the islet survival is improved as a result of such administration, it is also safe to conclude that the agents "suppress damage to transplanted islets" after islet transplantation. Islet survival can be assessed by determining whether or not normal blood sugar levels are restored following transplantation to diabetic recipients. For example, when 200 islets, which can be isolated from a single donor, are transplanted to the control group described in the Examples herein, the hyperglycemic state is maintained and thus viability can be regarded as 0%. However, when the same number of islets as used for the control group is transplanted to the anti-IL-6 receptor antibody-administered group described in the Examples herein, normal blood sugar levels are restored to all recipients, and thus the viability is regarded as 100%.

All prior-art documents cited herein are incorporated herein by reference.

EXAMPLES

Hereinbelow, the present invention will be specifically described with reference to the Examples, but it is not to be construed as being limited thereto.

Example 1

Investigation into the Suppression of Damage to Transplanted Islets after Transplantation of Isogenic Islets, where the Effect is Due to Administration of Anti-IL-6 Receptor Antibodies Diabetic recipient mice were prepared by intravenously administering streptozotocin (180 mg/kg) to male C57BL/6 mice. Streptozotocin is an agent that selectively destroys pancreatic Langerhans islets. A single administration of streptozotocin eliminates the majority of B cells, and thus induces type 1 diabetes.

Without islet transplant, all mice maintained hyperglycemic states (FIG. 1). Three to five days after streptozotocin administration, isolated isogenic mouse islets were transplanted to the livers of diabetic mice via the portal vein. The islets were isolated from donor pancreas using the collagenase-based methods.

Figure 2:
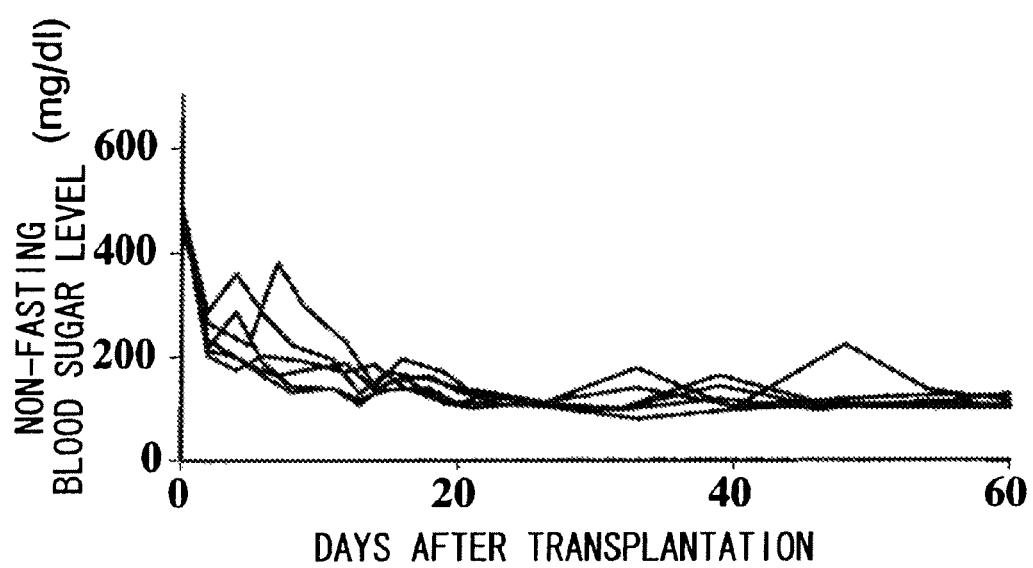
FIG. 2 is a graph showing changes in blood sugar levels in diabetic recipient mice that received isogenic transplantation of islets from the pancreases of two mice (400 islets).

200 islets can be isolated from a single mouse pancreas. In the case of 400 donor islets from two mice, normal blood sugar levels were restored after transplantation to diabetic recipients, and the diabetes could be treated (FIG. 2).

In this Example, blood was collected from the orbital sinus, and blood sugar levels were determined using a Beckman Glucose Analyzer after plasma skimming.

Figure 3:
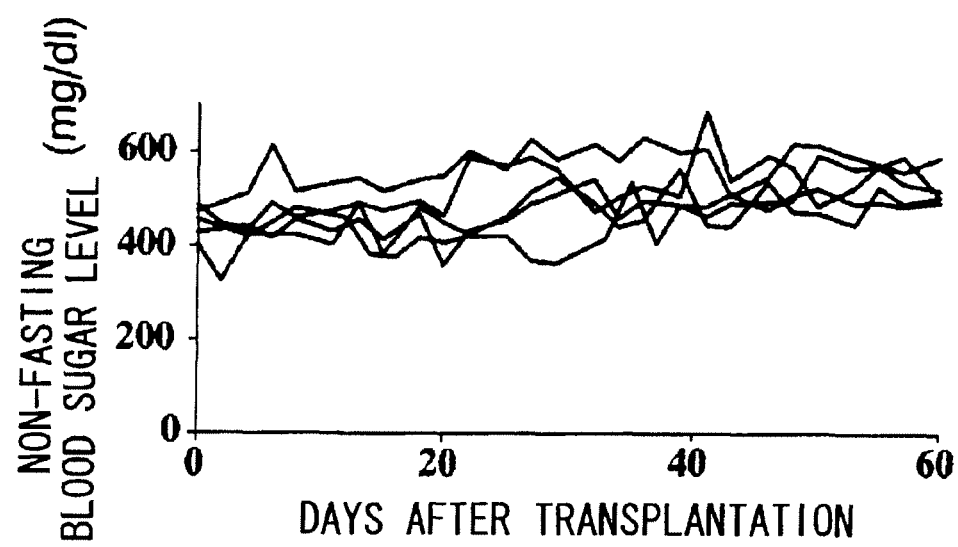
FIG. 3 is a graph showing changes in blood sugar levels in diabetic recipient mice that received isogenic transplantation of islets from a single mouse pancreas (200 islets).

However, transplantation of 200 islets from one mouse did not restore normal blood sugar levels and the recipients maintained hyperglycemic states (FIG. 3).

Figure 4:
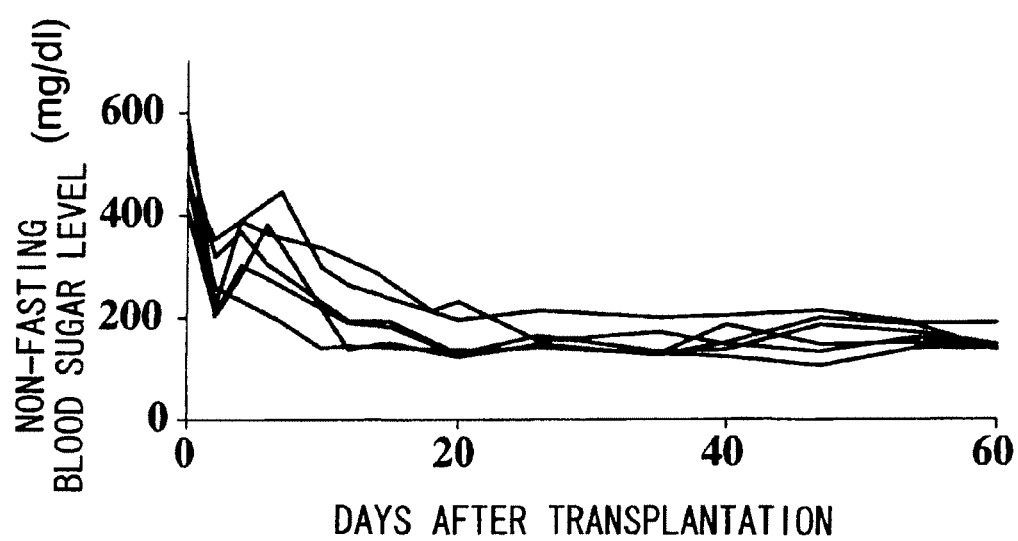
FIG. 4 is a graph showing changes in blood sugar levels in diabetic recipient mice that received isogenic transplantation of islets from a single mouse pancreas (200 islets), and were intraperitoneally administered three times with 500 μg of anti-IL-6 receptor antibody after transplantation.
Figure 5:
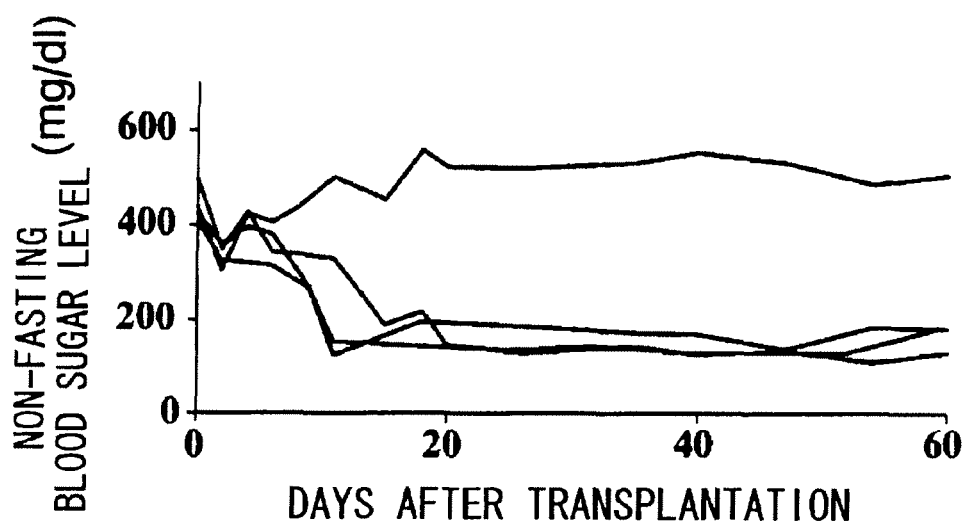
FIG. 5 is a graph showing changes in blood sugar levels in diabetic recipient mice that received isogenic transplantation of islets from a single mouse pancreas (200 islets), and were intraperitoneally administered once with 500 μg of anti-IL-6 receptor antibody after transplantation.
Figure 6:
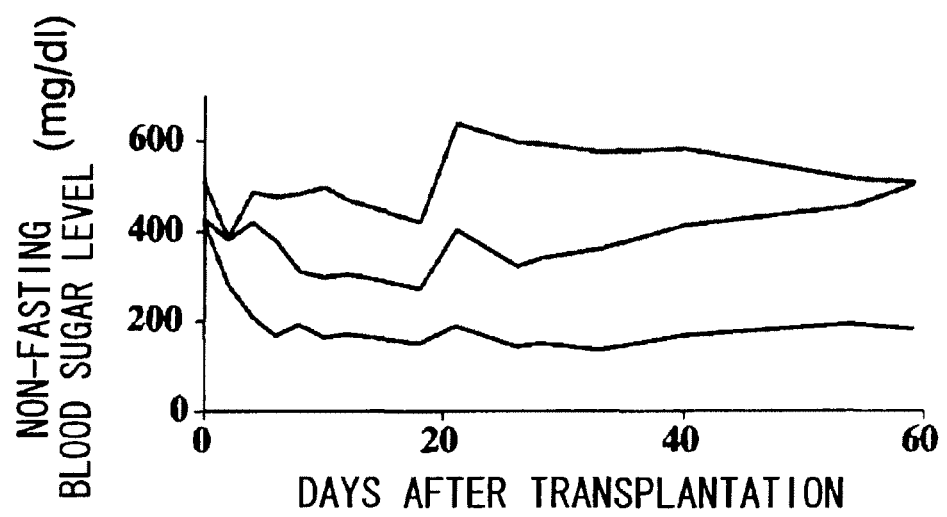
FIG. 6 is a graph showing changes in blood sugar levels in diabetic recipient mice that received isogenic transplantation of islets from a single mouse pancreas (200 islets), and were intraperitoneally administered once with 200 μg of anti-IL-6 receptor antibody after transplantation.

When 500 μg of anti-IL-6 receptor antibody (MR16-1) was intraperitoneally administered three times after transplantation of 200 islets (days 0, 2, and 4), normal blood sugar levels were restored in all recipients after transplantation (FIG. 4). When an equal dose of anti-IL-6 receptor antibody was administered once, normal blood sugar levels were restored in three-quarters of recipients (FIG. 5). Alternatively, when 200 μg of anti-IL-6 receptor antibody was administered once, normal blood sugar levels were restored in one-third of recipients (FIG. 6).

The above results show that anti-IL-6 receptor antibodies reduced damage to transplanted islets, improved islet survival, and corrected hyperglycemia in recipients. Specifically, it was found that anti-IL-6 receptor antibodies can be used as agents for suppressing damage to transplanted islets after isogenic islet transplantation (isografts).

Example 2

Investigation into the Suppression of Inflammatory Cytokine Production, where the Effect is Due to Administration of Anti-IL-6 Receptor Antibodies Flow cytometry assay methods were used to investigate whether administration of the anti-IL-6 receptor antibodies of the present invention suppressed the post-transplantation production of inflammatory cytokines by infiltrating cells.

Figure 7:
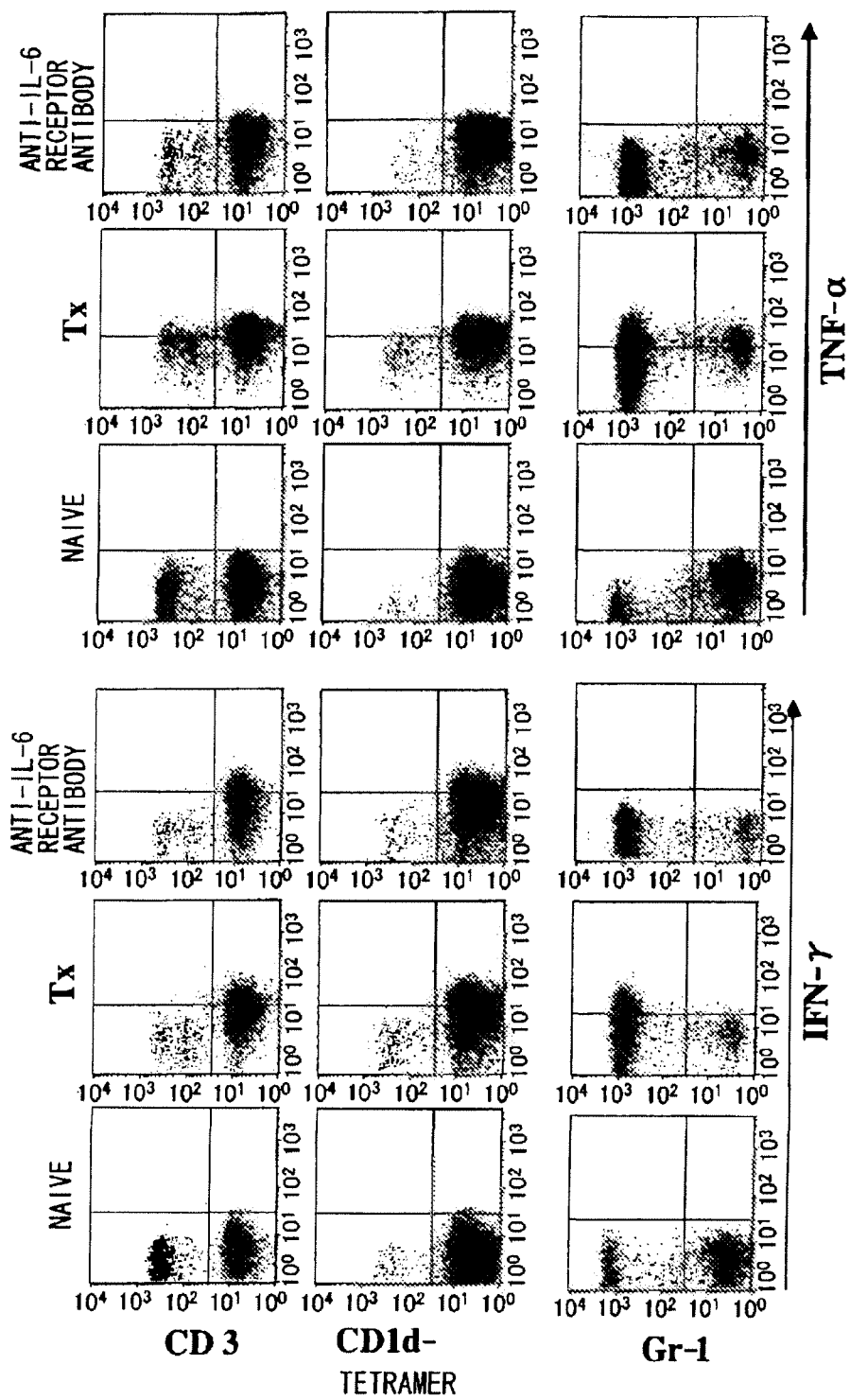
FIG. 7 is a graph showing that the administration of anti-IL-6 receptor antibody suppresses post-transplantation production of inflammatory cytokines by infiltrating cells.

200 isogenic islets were transplanted to the livers of streptozotocin-diabetic mice, and after six hours the animals were sacrificed, their livers were excised, and hepatic mononuclear cells were isolated and analyzed by flow cytometry (FIG. 7).

IFN-γ and TNF-α production was not observed in hepatic mononuclear cells from untreated (naïve) mice. IFN-γ and TNF-α production was enhanced in hepatic mononuclear cells from the control group, which was not administered with anti-IL-6 receptor antibodies. IFN-γ and TNF-α production was not observed in the hepatic mononuclear cells of mice to which anti-IL-6 receptor antibodies were administered once (ip; 200 μg/injection/mouse) at the time of transplantation. These findings suggest that administration of anti-IL-6 receptor antibodies prevents damage to transplanted islets by suppressing the production of inflammatory cytokines.

Example 3

Investigation into the Suppression of Damage to Transplanted Islets in Allogenic Islet Transplantation, where the Effect is Due to Administration of Anti-IL-6 Receptor Antibodies Diabetic recipient mice were prepared by intravenously administering streptozotocin (180 mg/kg) to male C57BL/6 mice. Three to five days after streptozotocin administration, isolated allogenic mouse (BALB/c) islets were transplanted to the livers of diabetic mice via the portal vein. Islets were isolated from donor pancreas using collagenase-based methods. Blood sugar levels were determined by the same method as described in Example 1.

Figure 8:
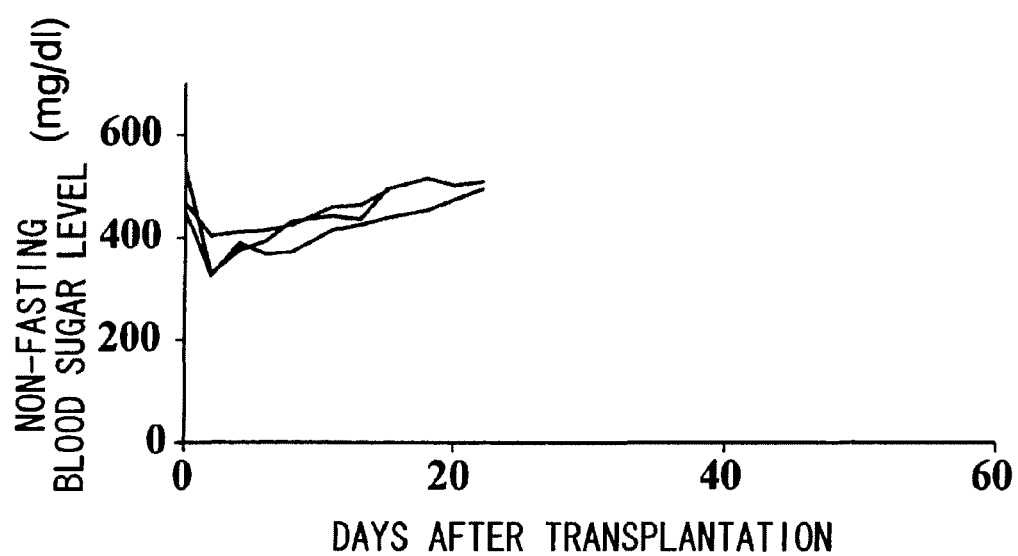
FIG. 8 is a graph showing changes in blood sugar levels in diabetic recipient mice that received allogenic transplantation of islets from a single mouse pancreas (200 islets), and were intraperitoneally administered three times with 200 μg of rat IgG after transplantation.
Figure 9:
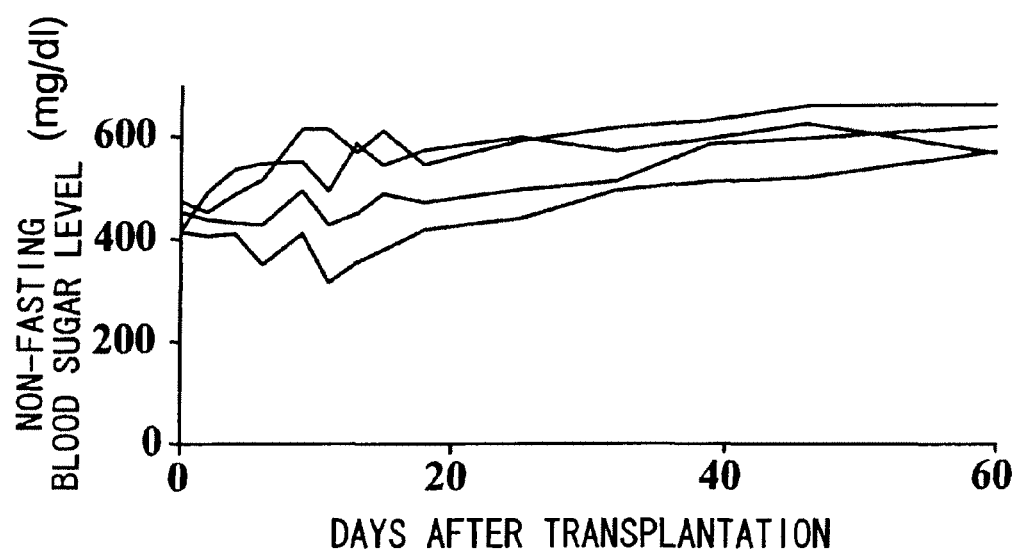
FIG. 9 is a graph showing changes in blood sugar levels in diabetic recipient mice that received allogenic transplantation of islets from a single mouse pancreas (200 islets), and were intraperitoneally administered once with 200 μg of anti-CD4 antibody after transplantation.
Figure 10:
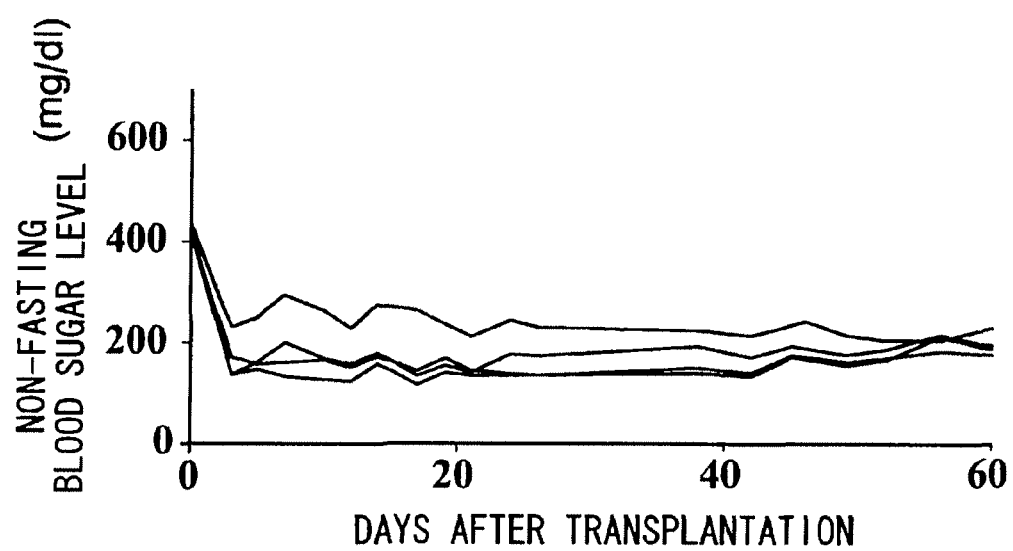
FIG. 10 is a graph showing changes in blood sugar levels in diabetic recipient mice that received allogenic transplantation of islets from a single mouse pancreas (200 islets) and were intraperitoneally administered three times with 500 μg of anti-IL-6 receptor antibody and once with 200 μg of anti-CD4 antibody after transplantation.

After the transplantation of 200 islets, 500 μg of anti-IL-6 receptor antibody (MR16-1) was intraperitoneally administered three times (days 0, 2, and 4), and 200 μg of anti-CD4 antibody was intraperitoneally administered once at the same tame as the first administration of anti-IL-6 receptor antibody, and normal blood sugar levels were restored in all recipients after the transplantation (FIG. 10). On the other hand, when 500 μg of a control antibody (rat IgG) (FIG. 8), or 200 μg of anti-CD4 antibody alone (FIG. 9), was administered the same number of times, all mice maintained hyperglycemic states.

The above results show that in recipients receiving allografts, the anti-IL-6 receptor antibodies also reduced damage to transplanted islets, improved islet survival, and corrected hyperglycemia. Specifically, it was found that the anti-IL-6 receptor antibodies can be used as agents for suppressing damage to transplanted islets after allogenic islet transplantations.

INDUSTRIAL APPLICABILITY

The methods and agents of the present invention for suppressing damage to transplanted islets improve islet survival after islet transplantation, and are expected to enable efficient diabetes treatment using fewer donor islets.

Previously, when transplanting islets isolated from pancreases of brain-dead donors or donors under cardiac arrest, a single recipient required islets isolated from the pancreases of two to three donors, since functional failure of islets was induced, which reduced graft viability. By using the agents of the present invention for suppressing damage to transplanted islets, the number of islets required by a single recipient is reduced, and as a result, more recipients are expected to be able to receive islet transplantations.

Recent reports describe successful cases of living donor islet transplantation, in which islets are isolated and purified from a portion of pancreas excised from healthy donors and transplanted to diabetes patients; however, use of the agents of the present invention for suppressing damage to transplanted islets is thought to enable the establishment of therapeutic methods that are less invasive for donors.

The invention claimed is:

1. A method for suppressing damage to a transplanted islet in an islet transplantation subject, the method comprising administering to the subject an antibody that recognizes an interleukin-6 (IL-6) receptor, thereby suppressing damage to the transplanted islet in the subject.

2. The method of claim 1, wherein the islet was isolated from a pancreas.

3. The method of claim 1, wherein the islet was transplanted into the subject's liver.

4. The method of claim 1, wherein the antibody is a monoclonal antibody.

5. The method of claim 1, wherein the antibody is an anti-human IL-6 receptor antibody.

6. The method of claim 1, wherein the antibody is a recombinant antibody.

7. The method of claim 1, wherein the antibody is a chimeric, humanized, or human antibody.

8. A method for suppressing damage to a transplanted islet in an islet transplantation subject, the method comprising administering to the subject an antigen-binding fragment of an antibody that recognizes an IL-6 receptor, thereby suppressing damage to the transplanted islet in the subject.

9. The method of claim 8, wherein the antigen-binding fragment is a Fab fragment or F(ab')2 fragment.

10. The method of claim 8, wherein the islet was isolated from a pancreas.

11. The method of claim 8, wherein the islet was transplanted into the subject's liver.

12. A method for suppressing damage to a transplanted islet in an islet transplantation subject, the method comprising administering to the subject an anti-IL-6 receptor Fv or an anti-IL-6 receptor scFv, thereby suppressing damage to the transplanted islet in the subject.

13. The method of claim 12, wherein the islet was isolated from a pancreas.

14. The method of claim 12, wherein the islet was transplanted into the subject's liver.

15. A method for improving viability of an islet in an islet transplantation subject, the method comprising administering to the subject an antibody that recognizes an IL-6 receptor, thereby improving viability of the islet in the subject.

16. The method of claim 15, wherein the islet was isolated from a pancreas.

17. The method of claim 15, wherein the islet was transplanted into the subject's liver.

18. The method of claim 15, wherein the antibody is a monoclonal antibody.

19. The method of claim 15, wherein the antibody is an anti-human IL-6 receptor antibody.

20. The method of claim 15, wherein the antibody is a recombinant antibody.

21. The method of claim 15, wherein the antibody is a chimeric, humanized, or human antibody.

22. A method for improving viability of an islet in an islet transplantation subject, the method comprising administering to the subject an antigen-binding fragment of an antibody that recognizes an IL-6 receptor, thereby improving viability of the islet in the subject.

23. The method of claim 22, wherein the antigen-binding fragment is a Fab fragment or F(ab')2 fragment.

24. The method of claim 22, wherein the islet was isolated from a pancreas.

25. The method of claim 22, wherein the islet was transplanted into the subject's liver.

26. A method for improving viability of an islet in an islet transplantation subject, the method comprising administering to the subject an anti-IL-6 receptor Fv or an anti-IL-6 receptor scFv, thereby improving viability of the islet in the subject.

27. The method of claim 26, wherein the islet was isolated from a pancreas.

28. The method of claim 26, wherein the islet was transplanted into the subject's liver.

* * * * *

UNITED STATES PATENT AND TRADEMARK OFFICE
CERTIFICATE OF CORRECTION

PATENT NO. : 8,470,316 B2
APPLICATION NO. : 12/090061
DATED : June 25, 2013
INVENTOR(S) : Yohichi Yasunami It is certified that error appears in the above-identified patent and that said Letters Patent is hereby corrected as shown below:

Title Page, Item (73) Assignee: Add -- Fukuoka University, Fukuoka (JP) --

Signed and Sealed this
Fifteenth Day of October, 2013

Teresa Stanek Rea
*Deputy Director of the United States Patent and Trademark Office*